United States Patent
Nelson et al.

(10) Patent No.: US 9,034,574 B2
(45) Date of Patent: May 19, 2015

(54) AGENTS FOR REVERSING EPIGENETIC SILENCING OF GENES

(75) Inventors: William G. Nelson, Towson, MD (US); Srinivasan Yegnasubramanian, Baltimore, MD (US); Xiaohui Lin, Redlands, CA (US); Traci J. Speed, Baltimore, MD (US); Zachery Reichert, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1080 days.

(21) Appl. No.: 12/521,109

(22) PCT Filed: Dec. 21, 2007

(86) PCT No.: PCT/US2007/088634
§ 371 (c)(1),
(2), (4) Date: Dec. 11, 2009

(87) PCT Pub. No.: WO2008/083098
PCT Pub. Date: Jul. 10, 2008

(65) Prior Publication Data
US 2010/0093768 A1   Apr. 15, 2010

Related U.S. Application Data

(60) Provisional application No. 60/877,310, filed on Dec. 27, 2006.

(51) Int. Cl.
*A61K 31/4184* (2006.01)
*G01N 33/50* (2006.01)
*G01N 33/68* (2006.01)

(52) U.S. Cl.
CPC ........ *G01N 33/5011* (2013.01); *A61K 31/4184* (2013.01); *G01N 33/6875* (2013.01); *G01N 2500/00* (2013.01)

(58) Field of Classification Search
None
See application file for complete search history.

(56) References Cited

U.S. PATENT DOCUMENTS 5,552,277 A * 9/1996 Nelson et al. ................ 435/6.12
6,905,669 B2   6/2005 DiMartino
2003/0224040 A1  12/2003 Baylin

FOREIGN PATENT DOCUMENTS

WO   WO 2004001027 A1 * 12/2003

OTHER PUBLICATIONS

Bakker et al. Methyl-CpG binding domain protein 2 represses transcription from hypermethylated pi-class glutathione S-transferase gene promoters in hepatocellular carcinoma cells. The Journal of Biological Chemistry, vol. 277, No. 25, pp. 22573-22580, 2002.*
Lin et al. Methyl-CpG-binding domain protein-2 mediates transcriptional repression associated with hypermethylated GSTP1 CpG islands in MCF-7 breast cancer cells. Cancer Research, vol. 63, pp. 498-504, 2003.*
Berger et al. Role of MBD2 in gene regulation and tumorigenesis. Stem Cells and Development, vol. 33, No. 6, pp. 1537-1539, 2005.*
Ballestar et al. Methyl-CpG binding proteins identify novel sites of epitgenetic inactivation in human cancer. The EMBO Journal, vol. 22, No. 23, pp. 6335-6345, 2003.*
Esteller et al. A gene hypermethylation profile of human cancer. Cancer Research, vol. 61, pp. 3225-3229, 2001.*
Townsend et al. The role of glutathione-S-transferase in anti-cancer drug resistance. Oncogene, vol. 22, pp. 7369-7375, 2003.*
Dang et al. Glutathione S-transferase Pi1 promoters tumorigenicity in HCT116 human colon cancer cells. Cancer Research, vol. 65, No. 20, pp. 9485-9494, Oct. 2005.*
Duvoix et al. Induction of apoptosis by curcumin: mediation by glutathione S-transerase P1-1 inhibition. Biochemical Pharmacology, vol. 66, No. 8, pp. 1475-1483, Oct. 2003.*
Uchida et al. MiR-133a induces apoptosis through direct regulation of GSTP1 in bladder cancer cell lines. Urologic Oncology: Seminars and Original Investigations, vol. 31, pp. 115-123, 2103.*
Woodson et al. Heterogeneous gene methylation patterns among pre-invasive and cancerous lesions of the prostate: A histopathologic study of whole mount prostate specimens. The Prostate, vol. 60, pp. 25-31, 2004.*
Hokaiwado et al. Glutathione S-transferase Pi mediates proliferation of androgen-independent prostate cancer cells. Carcinogenesis, vol. 29, No. 6, pp. 1134-1138, 2008.*
Naiki et al. Organ specific Gst-pi expression of the metastatic androgen independent prostate cancer cells in nude mice. The Prostate, vol. 72, pp. 533-541, 2012.*
Lin et al. Reversal of GSTP1 CpG island hypermethylation and reactivation of Pi-class glutathione S-transferase (GSTP1) expression in human prostate cancer cells by treatment with procainamide. Cancer Research, vol. 61, pp. 8611-8616, Dec. 2001.*
Huang et al. Prognostic significance of glutathione S-tansferase-Pi in invasive breast cancer. Modern Pathology, vol. 16, No. 6, pp. 558-565, 2003.*
Pace and Zein, "Understanding Mechanisms of γ-Globin Gene Regulation to Develop Strategies for Pharmacological Fetal Hemoglobin Induction," Developmental Dynamics,235:1727-1737, Wiley-Liss, Inc. (2006).

* cited by examiner

*Primary Examiner* — Jennifer Dunston
(74) *Attorney, Agent, or Firm* — DLA Piper LLP (US)

(57) ABSTRACT

The present invention provides methods for discovering agents that are effective in reversing epigenetic silencing by inhibiting the interaction of methyl-binding (MBD) proteins with methylated genomic DNA. Also provided are methods for reactivating silenced genes having CpG island hypermethylation along with methods for treatment and prevention of diseases, such as cancer and sickle cell anemia, by administering an agent that modulates methyl-binding domain (MBD) protein-mediated transcriptional repression, thereby increasing gene transcription to prevent or treat disease. Additionally, compounds identified by the present invention useful for treatment and prevention of diseases, such as cancer and sickle cell anemia, are provided.

8 Claims, 18 Drawing Sheets

FIG. 3

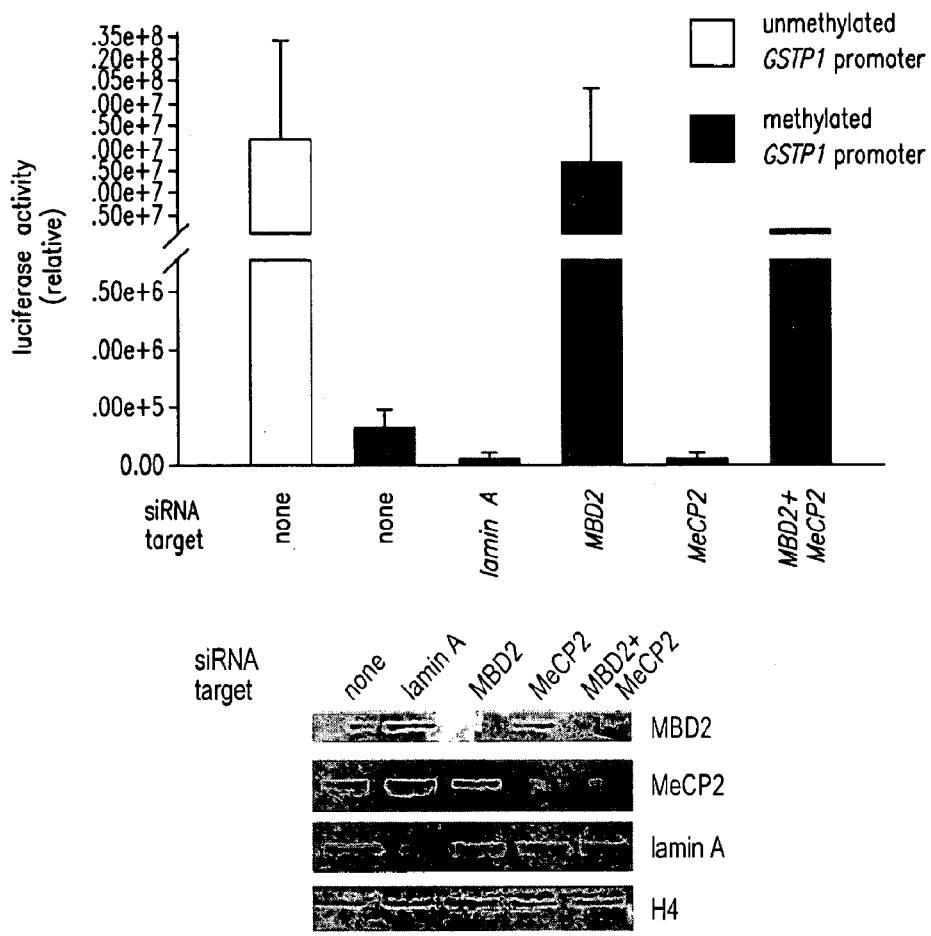

FIG. 11

Stage 1 screening for MBD2 pathway antagonists:

Simultaneous transfection of methylated and unmethylated GSTP1 promoters ligated to different reporter genes

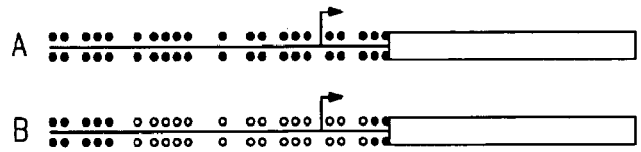

Possible outcomes:

↓A or no change in A → no further interest

↑A and no change in B → possible MDB2 pathway antagonist

↑A and ↑B → likely general transcription regulation pathway activator/no further interest

FIG. 12

AGENTS FOR REVERSING EPIGENETIC SILENCING OF GENES

CROSS REFERENCE TO RELATED APPLICATIONS

This application is a 35 USC §371 National Stage application of International Application No. PCT/US2007/088634 filed Dec. 21, 2007, now pending; which claims the benefit under 35 USC §119(e) to U.S. Application Ser. No. 60/877,310 filed Dec. 27, 2006. The disclosure of each of the prior applications is considered part of and is incorporated by reference in the disclosure of this application.

GRANT INFORMATION

This invention was made with government support under Grant No. R01 CA113374 awarded by the National Institutes of Health, National Cancer Institute. The government has certain rights in the invention.

BACKGROUND OF THE INVENTION

1. Field of the Invention

The invention relates generally to the field of DNA methylation and more specifically to the use and detection of agents that reverse epigenetic "silencing" of genes resulting from DNA hypermethylation.

2. Background Information

DNA methylation, or the covalent addition of a methyl group to cytosine within the context of the CpG dinucleotide, has profound effects on the mammalian genome. These effects include transcriptional repression via inhibition of transcription factor binding or the recruitment of methyl-binding proteins and their associated chromatin remodeling factors, X chromosome inactivation, imprinting and the suppression of parasitic DNA sequences. DNA methylation is also essential for proper embryonic development; however, its presence can add an additional burden to the genome. Normal methylation patterns are frequently disrupted in tumor cells with global hypomethylation accompanying region-specific hypermethylation. When these hypermethylation events occur within the promoter of a tumor suppressor gene they may silence the gene and provide the cell with a growth advantage in a manner akin to deletions or mutations. Furthermore, DNA methylation may be an important player in both DNA repair and genome stability.

DNA methylation at the 5-position of cytosine in CpG dinucleotides is an important aspect of physiological processes, such as embryonic development, X chromosome inactivation, imprinting, and transcriptional regulation. While CpG dinucleotides are generally methylated throughout the genome of normal somatic cells, CpG islands (CGIs), clusters of CpG dinucleotides in gene regulatory regions, are usually unmethylated.

Epigenetic gene "silencing" occurs in cancer cells. Of all the somatic genome changes that accumulate during the pathogenesis of human cancer, only changes in DNA methylation appear to occur consistently (virtually all cases), to arise early (first appearing in preneoplastic lesions), and to be potentially reversible (the DNA sequence remains intact). One such change in DNA methylation, increased CpG dinucleotide methylation at CpG islands encompassing the transcriptional regulatory regions of many genes, leads to the transcriptional "silencing" of critical cancer genes. Aberrant hypermethylation of CGIs and subsequent transcriptional repression is one of the earliest and most common somatic genome alterations in multiple human cancers.

CpG island hypermethylation has been reported to inhibit gene transcription by interfering with the binding and/or function of transcriptional transactivators, or by recruiting [5-m] CpG-binding domain (MBD) family proteins capable of mediating transcriptional repression via effects on chromatin structure. As an example, for the GSTP1 CpG island hypermethylated in cancers, such as prostate, breast, and liver cancers, the MBD family protein MBD2 has been found responsible for methylation-associated "silencing" of gene transcription.

Somatic CpG island hypermethylation and associated gene "silencing" may be effectively targeted for rational cancer treatment and prevention. One strategy, under current clinical development, features the use of inhibitors of DNA methyltransferases (DNMTs), such as 5-aza-cytdine, 5-aza-deoxycytidine, zebularine, procainamide, or hydralazine, to reduce [5-m]CpG density at the CpG island sequences in dividing cancer cells. Another approach, also under active clinical development, has been the use of inhibitors of histone deacetylases (HDACs), such as sodium phenylbutyrate, valproic acid, or suberoylanilide hydroxamic acid (SAHA), to limit the formation of repressive chromatin conformation near the genes caring abnormally methylated CpG islands.

Nucleoside analog inhibitors of DNMTs, such as 5-azcytidine (5-aza-C) and 5-aza-deoxycytidine (5-aza-dC), have been widely used in attempts to reverse abnormal DNA methylation changes in cancer cells and restore "silenced" gene expression. Unfortunately, despite some apparent successes using pre-clinical models and some promising results in early clinical trials (Table 1), the clinical utility of these compounds for cancer has not yet been fully realized and the drugs have not yet been approved by the U.S. Food and Drug Administration (F.D.A.) for any indication.

TABLE 1

Nucleoside DNMT Inhibitors and Solid Tumors

| Tumor | Agent | n | Dose/Schedule/Route | % Response |
|---|---|---|---|---|
| breast ca | 5-aza-C | 11 | 300-700 mg/M$^2$ over 8 days iv | 63 |
| | 5-aza-C | 31 | 600 mg/M$^2$ over 10 days iv | 6 |
| | 5-aza-C | 4 | 275-850 mg/M$^2$ over 10 days sq | 25 |
| | 5-aza-C | | 1.6 mg/kg over 10 days iv | 17 |
| ovarian ca | 5-aza-C | 4 | 275-850 mg/M$^2$ over 10 days sq | 25 |
| | 5-aza-dC | 24 | 225 mg/M$^2$ over 10 days iv | 8 |
| colon ca | 5-aza-C | 27 | | 4 |
| | 5-aza-C | 6 | 300-700 mg/M$^2$ over 10 days iv | 33 |
| | 5-aza-C | 4 | 275-850 mg/M$^2$ over 8 days sq | 0 |
| | 5-aza-dC | 42 | 225 mg/M$^2$ over 1 day iv | 0 |
| lung ca | 5-aza-dC | 15 | 200-600 mg/M$^2$ over 1 day iv | 20 |
| prostate ca | 5-aza-dC | 14 | 225 mg/M$^2$ over 1 day iv | 16 |
| melanoma | 5-aza-C | 5 | 300-700 mg/M$^2$ over 8 days iv | 40 |
| | 5-aza-dC | 18 | 225 mg/M$^2$ over 1 day iv | 0 |
| | dh-5-aza-C | 40 | 5 g/M$^2$ over 1 day cl | 20 |
| mesothelioma | dh-5-aza-C | 41 | 1500 mg/M$^2$ over 5 days cl | 17 |
| | dh-5-aza-C | 29 | 1500 mg/M$^2$ over 5 days cl | 17 |

One of the limitations of the nucleoside analog DNMT inhibitors in clinical trials has been treatment-associated side effects, such as myelotoxicity with resultant neutropenia and thrombocytopenia, which are characteristic of other nucleoside analogs in general, including nucleoside analogs that are not DNMT inhibitors.

Another concern about the use of nucleoside analogs as DNMT inhibitors has been that incorporation of the nucleoside analogs into genomic DNA might lead to mutations and/or cancer development. Procainamide, a drug approved by the F.D.A. for the treatment of cardiac arrhythmias, and hydralazine, a drug approved for the treatment of hypertension, are non-nucleoside analogs that both also appear to inhibit DNMTs. However, long-term use of either of these drugs caries a risk of drug-induced lupus, more commonly in women than in men. In animal models, both 5-aza-C and procainamide appear to trigger autoimmunity, though whether or not autoimmunity is an unavoidable side effect of DNMT inhibition is not known. Finally, mice carrying one disrupted DNMT1 allele and one hypomorphic DNMT1 allele, resulting in 10% of normal DNMT activity, have been reported to exhibit genomic instability and to develop T-cell lymphomas, hinting that therapeutic reductions in $^{5-m}CpG$ dinucleotides might promote the appearance of certain cancers (eg. lymphomas) while attenuating the appearance of others. Thus, the clinical use of DNMT inhibitors is likely to be limited by both mechanism-based and mechanism-independent side effects.

Like DNMT inhibitors, HDAC inhibitors have also exhibited promising preclinical activity in cancer models. HDAC inhibitors under clinical development include sodium phenyl butyrate (and other butyrates), valproic acid, suberoylanilide hydroxamic acid (SAHA), pyroxamide, N-acetyl dinaline (CI-994), and depsipeptide. However, the early clinical experience with these agents suggests that side effects, such as nausea, vomiting, diarrhea, fatigue, edema, etc., can occur, though severe adverse events appear rare. In addition to DNMT inhibitors and HDAC inhibitors given as single agents, combinations of DNMT inhibitors and HDAC inhibitors also appear to have intriguing activity in preclinical models. Whether combinations of the currently available collection of DNMT inhibitors and HDAC inhibitors can reactivate silenced cancer genes, without unacceptable toxicity, in human clinical trials, has not yet been determined.

In addition to treatment and prevention of cancer, reactivation of silenced genes may be useful for treatment of other diseases, such as sickle cell anemia. Sickle cell anemia is caused by a point mutation in the beta-globin gene (HBb). Dimers of this mutant form of HBb multimerize with dimers of alpha-globin (Hba) to make sickle hemoglobin (HBs). HBs is prone to polymerization, causing sickling of red blood cells, and subsequent aberrant interactions between the sickled red blood cells, immune cells, and endothelial cells that result in a complex spectrum of disease manifestations. Reactivation of the gamma-globin gene, presents a useful strategy in treatment of sickle cell disease.

SUMMARY OF THE INVENTION

The present invention is based in part on the seminal discovery of compounds that reverse epigenetic silencing. It is believed that these agents function by inhibiting the interaction of a methyl-binding domain (MBD) protein with methylated genomic DNA. Accordingly, the present invention provides a method of screening for an agent that inhibits the interaction of a methyl-binding domain (MBD) protein with methylated genomic DNA.

In one embodiment, the present invention provides a method of screening for an agent that inhibits the interaction of a methyl-binding domain (MBD) protein with methylated genomic DNA. The method includes contacting a sample comprising an MBD protein, an MBD protein-mediated gene having hypermethylated CpG islands and an MBD protein-mediated gene having non-hypermethylated CpG islands, with a test agent under conditions sufficient for transcription of the MBD protein-mediated gene, detecting the transcriptional activity of the MBD protein-mediated gene, and comparing the difference in transcriptional activity between the MBD protein-mediated gene having hypermethylated CpG islands and the MBD protein-mediated gene having non-hypermethylated CpG islands in the presence and absence of the test agent. An increase in transcription of the MBD protein-mediated gene having hypermethylated CpG islands as compared to the MBD protein-mediated gene having non-hypermethylated CpG islands, in the presence of the agent, identifies the agent as an inhibitor of the interaction of a methyl-binding domain (MBD) protein with methylated genomic DNA.

In one aspect, the agent is a chemical compound. In another aspect the agent is a chemical compound selected from those shown in Table 2.

In another aspect, the method further includes determining whether the identified agent is also an inhibitor of a DNA methyltransferase (DNMT) protein by testing the ability of the compound to inhibit DNA methylation. In another embodiment, the MBD protein is methyl-CpG binding domain protein 2 (MBD2) or methyl CpG binding protein 2 (MeCP2).

In another aspect, the MBD protein mediated gene includes a promoter region. In another embodiment, the promoter region is a GSTP1 promoter. In another aspect, the MBD protein mediated gene further includes a reporter gene or reporter molecule. In another aspect, the reporter molecule is selected from radionuclides, enzymes, fluorescent, chemiluminescent, or chromogenic agents as well as substrates, cofactors, inhibitors, or magnetic particles.

In another embodiment, the invention provides a method of preventing or treating cancer associated with CpG island hypermethylation of a gene in a subject. The method includes administering to the subject an agent that modulates methyl-binding domain (MBD) protein-mediated transcriptional repression, thereby increasing transcription of the gene and thereby preventing or treating the cancer. In one aspect, the gene is selected from GSTP1, APC, HIC-1, RASSF1A, PTGS-2, EDNRB, ESR1, TIMP3, CDKN2A, CDKN2B, MLH1, MGMT, DAPK1, CDH1, ARF, IGF2, H19, p57/KIP2, KvLQT1, TSSC3, TSSC5, or ASCL2. In one example, the MBD protein is MBD2 or MeCP2. The cancer may be selected from colorectal cancer, esophageal cancer, stomach cancer, leukemia/lymphoma, lung cancer, prostate cancer, uterine cancer, breast cancer, skin cancer, endocrine cancer, urinary cancer, pancreatic cancer, other gastrointestinal cancer, ovarian cancer, cervical cancer, head cancer, neck cancer, kidney cancer, liver cancer, bladder cancer, breast cancer or adenomas.

In another embodiment, the invention provides a method of preventing or treating sickle cell anemia in a subject. The method includes administering to the subject an agent that modulates methyl-binding domain (MBD) protein-mediated transcriptional repression, thereby preventing or treating the sickle cell anemia. For example, the MBD protein is MBD2 or MeCP2.

In another embodiment, the invention provides a method of reactivating a silenced gene having CpG island hypermethylation. The method includes contacting a cell with an agent that modulates methyl-binding domain (MBD) protein-mediated transcriptional repression, thereby increasing transcription of the silenced gene. For example, the agent is an inhibitor of the interaction of a methyl-binding domain (MBD) protein with methylated genomic DNA. In one aspect, the agent is a chemical compound. For example, the agent may be a chemical compound selected from those shown in Table 2.

BRIEF DESCRIPTION OF THE DRAWINGS

FIG. 3 is a graphical representation showing a CpG island methylation index for metastatic prostate cancers, showing greater differences in methylation patterns between cases than between metastatic deposits.

FIG. 11 is a graphical representation and pictorial diagram showing siRNA-mediated "knock-down" of MBD2 alleviates repression of methylated GSTP1 promoters in transient transfection assays.

FIG. 12 is a pictorial diagram illustrating the stage 1 screening assay for MBD2 pathway antagonists.

FIG. 18 is a pictorial representation showing the production and purification of recombinant DNA methyltransferases. Shown are the results of baculovirus mediated expression of DNMT1 and DNMT3a.

FIG. 19 is a graphical representation of Lineweaver-Burk analysis of procainamide inhibition of DNMT3a.

DETAILED DESCRIPTION OF THE INVENTION

Figure 1:
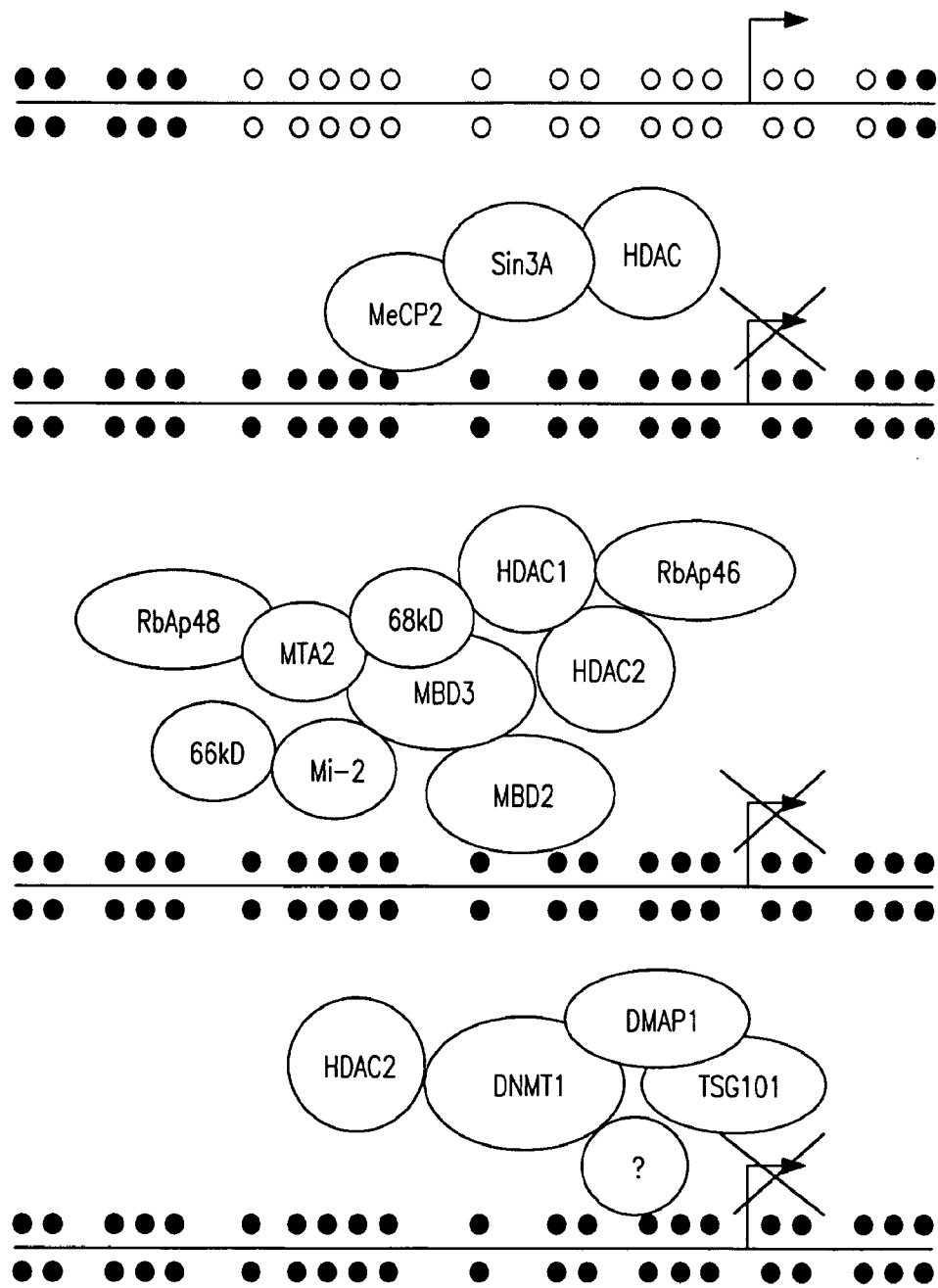
FIG. 1 shows a pictorial diagram illustrating how $^{5-m}$CpG-binding domain (MBD) family proteins recruit transcription repression complexes to hypermethyated CpG islands to "silence" critical cancer genes.

The present invention provides methods for using and identifying agents that are effective in reversing epigenetic silencing. It is believed that such agents inhibit the interaction of a methyl-binding domain (MBD) protein with methylated genomic DNA thereby reversing epigenetically silenced genes.

Of all the somatic genome changes that accumulate during the pathogenesis of human cancer, changes in DNA methylation appear to occur consistently, to arise early, and to be potentially reversible. One such change in DNA methylation, increased CpG dinucleotide methylation at CpG islands encompassing the transcriptional regulatory regions of many genes, leads to the transcriptional "silencing" of critical cancer genes. CpG island hypermethylation has been reported to inhibit gene transcription by interfering with the binding and/or function of transcriptional transactivators, or by recruiting $^{5-m}$CpG-binding domain (MBD) family proteins capable of mediating transcriptional repression via effects on chromatin structure.

One of the MBD family proteins, MeCP2, contains an approximately 70 amino acid minimal region that mediates selective binding to DNA containing $^{5-m}$CpG (an MBD motif), and a transcriptional repression domain (TRD) that permits interaction with the transcriptional repressor Sin 3 and associated HDACs. MeCP2 can thus act as a CpG island hypermethylation-dependent transcriptional repressor by binding transcriptional regulatory sequences carrying $^{5-m}$CpG and recruiting HDACs. For this reason, MeCP2-mediated inhibition of $^{5-m}$CpG-containing promoter activity can usually be alleviated by treatment with trichostatin A, an inhibitor of HDACs.

Another MBD family protein, MBD2, which can also bind selectively to DNA containing $^{5-m}$CpG, has been found to be a component of a 1 MD transcription repression complex, MeCP1, that also contains the Mi-2/NuRD chromatin remodeling complex subunits MBD3, HDAC1 and HDAC2, histone-binding proteins RbAp46 and RbAp48, the SWI/SNF helicase/ATPase domain-containing protein Mi2, MTA2, and two uncharacterized polypeptides of 66 and 68 kD.

Though present in the Mi-2/NuRD complex, the MBD family protein MBD3 does not appear to recognize $^{5-m}$CpG-containing DNA. As a result, in the absence of MBD2, Mi-2/NuRD complexes, capable of catalyzing ATP-dependent chromatin remodeling, are incapable of selectively binding hypermethylated transcriptional regulatory sequences. In the MeCP1 complex, MBD2 acts to recruit the Mi-2/NuRD chromatin remodeling complex to $^{5-m}$ CpG-containing DNA. Although MeCP2-mediated transcriptional repression can typically be alleviated by treatment with HDAC inhibitors, MeCP1-mediated inhibition of $^{5-m}$ CpG-containing promoter activity is often not affected by HDAC inhibitor exposure.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, the terms "sample" and "biological sample" refer to any sample suitable for the methods provided by the present invention. The sample can be any sample that may be used such that MBD protein activity can be detected. In one aspect, the sample is a biological sample, including, for example, a bodily fluid, an extract from a cell, which can be a crude extract or a fractionated extract, a chromosome, an organelle, or a cell membrane; a cell; genomic DNA, RNA, or cDNA, which can be in solution or bound to a solid support; a tissue; or a sample of an organ. A biological sample, for example, from a human subject, can be obtained using well known and routine clinical methods (e.g., a biopsy procedure).

The present invention describes agents, such as chemical compounds, and the processes and assays used for their identification, that target MBD proteins for the treatment and/or prevention of numerous human diseases, including multiple cancers and sickle cell anemia, in which disruption of MBD-DNA and MBD-Protein interactions is beneficial. Existing strategies for epigenetics-based therapies do not target MBD proteins, but rather they target the upstream DNA methyltransferase (DNMT) enzymes, and/or the downstream histone modifying enzymes.

One embodiment of the present invention provides methods for the identification of agents, such as chemical compounds, that are inhibitors of the transcriptional repression pathway mediated by the $^{5-m}$CpG-binding family domain (MBD) proteins MBD2 and MeCP2. Through the use of genetic experiments, both MBD2 and MeCP2 have been found to play critical roles both in the epigenetic "silencing" of genes, like GSTP1, in human cancer cells, and/or in the development of intestinal adenomas in Apc$^{Min/+}$ mice. Accordingly, the present invention involves, in part, the discovery of agents, that may be, for example, selective for MBD2-mediated transcriptional repression or capable of acting against both MBD2 and MeCP2, to reverse the epigenetic "silencing" of genes that are associated with cancer development.

MBD proteins play a role in transcriptional repression accompanying CpG island hypermethylation in cancer cells. Two MBD family proteins have been implicated in the silencing of critical genes in cancer cells carrying abnormally hypermethylated CpG island sequences (FIG. 1).

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

The terms "small interfering RNA" and "siRNA" also are used herein to refer to short interfering RNA or silencing RNA, which are a class of short double-stranded RNA molecules that play a variety of biological roles. Most notably, siRNA is involved in the RNA interference (RNAi) pathway where the siRNA interferes with the expression of a specific gene. In addition to their role in the RNAi pathway, siRNAs also act in RNAi-related pathways (e.g., as an antiviral mechanism or in shaping the chromatin structure of a genome).

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

The present invention is based, in part, on the finding that MBD2-containing complexes are responsible for transcriptional repression accompanying somatic CpG island hypermethylation at GSTP1, which is the most common somatic genome change yet reported for prostate cancer, and is also a common alteration in other cancers, such as breast and liver cancers.

Accordingly, in one embodiment, the present invention provides a method of screening for an agent capable of reversing epigenetic silencing by inhibiting the interaction of a methyl-binding domain (MBD) protein with methylated genomic DNA. In one embodiment the present invention provides a method for identifying an agent that inhibits the interaction of a methyl-binding domain (MBD) protein with methylated genomic DNA. The method includes screening for an agent that inhibits the interaction of an MBD protein with methylated DNA by contacting a sample comprising an MBD protein, an MBD protein-mediated gene having hypermethylated CpG islands and an MBD protein-mediated gene having non-hypermethylated CpG islands, with a test agent under conditions sufficient for transcription of the MBD protein-mediated gene, detecting the transcriptional activity of the MBD protein-mediated gene, and comparing the difference in transcriptional activity between the MBD protein-mediated gene having hypermethylated CpG islands and the MBD protein-mediated gene having non-hypermethylated CpG islands in the presence and absence of the test agent. An increase in transcription of the MBD protein-mediated gene having hypermethylated CpG islands as compared to the MBD protein-mediated gene having non-hypermethylated CpG islands, in the presence of the agent, identifies the agent as an inhibitor of the interaction of a methyl-binding domain (MBD) protein with methylated genomic DNA.

An agent useful in any of the methods of the invention can be any type of molecule, for example, a polynucleotide, a peptide, a peptidomimetic, peptoids such as vinylogous peptoids, chemical compounds, such as organic molecules or small organic molecules, or the like, and can act in any of various ways to inhibit the interaction of a methyl-binding domain (MBD) protein with methylated genomic DNA to treat diseases, such as cancer and sickle cell anemia. For example, the agent may be selective for MBD2-mediated transcriptional repression or capable of acting against MBD2 or MeCP2, to reverse the epigenetic "silencing" of critical genes that accompanies cancer development. Accordingly, in one aspect, an agent identified by the method of the present invention is a chemical compound. For example the agent is a chemical compound selected from those shown in Table 2. Compounds of the invention can be modified and derivatized at multiple functional groups to enhance pharmacokinetic, pharmacodynamic, and biochemical properties. Such methods are commonly known to those of skill in the art.

Test agents encompass numerous chemical classes, though typically they are chemical compounds, such as an organic molecule, and often are small organic compounds (i.e., small molecules) having a molecular weight of more than 100 Daltons and less than about 2,500 Daltons. Test agents comprise functional groups necessary for structural interaction with proteins, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In another aspect, the method further includes determining whether an agent identified by the present invention is an inhibitor of a DNA methyltransferase (DNMT) protein by testing the ability of the agent to inhibit DNA methylation. The agent may inhibit DNA methylation by DNMT proteins DNMT1, DNMT3a, and/or DNMT3b, in natural or recombinant forms, including fragments thereof.

It is known in the art that a variety of genes are involved in cancer, tumor, and metastasis. Many of these genes have been found to contain regions of DNA hypermethylation in diseased tissues, including cancer, and may be MBD protein-mediated genes. The list of imprinted genes continues to grow and includes at least 80 human and mouse genes. Such hypermethylated genes, include but are not limited to: GSTP1, APC, HIC-1, RASSF1A, PTGS-2, EDNRB, MDR-1, ESR1, TIMP3, CDKN2A, CDKN2B, MLH1, MGMT, DAPK1, CDH1, ARF, IGF2, H19, p57/KIP2, KvLQT1, TSSC3, TSSC5, and ASCL2, among others. Furthermore, for a majority of these genes, if not for all of these genes, the expression is regulated by methylation, and hence also by hypermethylation. Moreover, most of these genes, if not all or these genes, have multiple methylation sites, resulting in a fine-tuning of regulation, but also in aberration of regulation by hypermethylation. In short, a gene may have one or more methylation sites which may be subjected to hypermethylation. These methylation sites may be located in the promoter region, including the regulatory regions, and methylation sites may also be located in the coding regions, and outside coding regions.

Accordingly, any of the above listed genes may be used in the screening method of the present invention. An MBD protein-mediated gene as described herein, is any gene whose transcription is mediated by an MBD protein. The method of the present invention may employ the entire gene, or any portion thereof, such as the promoter. A "promoter" is a nucleic acid sequence that directs the binding of RNA polymerase and thereby promotes RNA synthesis. Promoter sequences include constitutive and inducible promoter sequences. Exemplary promoter sequences include promoters from MBD protein-mediated genes, such as GSTP1. The promoters can be either naturally occurring promoters, hybrid promoters, or synthetic promoters. Hybrid promoters, which combine elements of more than one promoter, are also known in the art, and are useful in the present invention.

An MBD protein-mediated gene may further include a reporter gene or reporter molecule to facilitate detecting the transcriptional activity of the MBD protein-mediated gene. For example, the present invention contemplates construction of promoter/reporter constructs. There are many genes and molecules that may be used in such a fashion, as well as methods of labeling known to those of ordinary skill in the art. Examples of the types of reporters known in the art includes radionuclides, enzymes, fluorescent, chemiluminescent, or chromogenic agents as well as substrates, cofactors, inhibitors, or magnetic particles. The reporter molecule or gene can be visibly observable or detectable using conventional detection techniques. In one embodiment the protein-mediated gene is a promoter/reporter construct including the promoter of a protein-mediated gene operably linked to a reporter gene, such as a *luciferase* gene. One illustrative example is a construct including a GSTP1 promoter operably linked to either a Firefly *luciferase* gene or a *Renilla luciferase* gene.

A nucleic acid is "operably linked" when it is placed into a functional relationship with another nucleic acid sequence. For example, DNA for a presequence or secretory leader is operably linked to DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the MBD polypeptide, as will be appreciated by those in the art; for example, transcriptional and translational regulatory nucleic acid sequences from Baculovirus are preferably used to express the MBD protein in cells. Numerous types of appropriate expression vectors, and suitable regulatory sequences are known in the art for a variety of host cells.

However, detection of the transcriptional activity of the MBD protein-mediated gene need not be through a promoter/reporter construct. For example, the transcriptional activity may be detected using other methods well known in the art, such as monitoring the activity utilizing GeneChip platforms to monitor expression profiles and transcriptional activity. Accordingly, the MBD protein-mediated gene is not required to include a reporter.

The screening method of the present invention may be performed on a number of platforms and utilize a variety of cell types. The method of the present invention may be performed, for example, on a solid support platform, or may be performed using a cell based assay. A variety of cells may be used, those known in the art and those commercially available, as well as those isolated from a subject. Thus, cells may be any type of cancer cell, including prostate cancer cells. Additionally, the method may be performed using cells transfected with an MBD protein-mediated gene or gene construct, such as described in the Examples. As such, the method is particularly suited to be performed in a high-throughput fashion, (e.g., 96-well plate analysis; mechanical or robotic processing).

The screening strategy of the present invention may employ chimeric polypeptides containing an affinity or epitope tag, such as a poly-His, GST, HA, Flag, myc, or other tag well known in the art. Such tags allow proteins to be conveniently isolated and purified through the interaction of the affinity or epitope tag with a cognate binding species, which can be a metal ion, glutathione, anti-HA antibody, anti-Flag antibody or anti-myc antibody, respectively, for the tags listed above. Furthermore, the affinity tag can be used to anchor the polypeptide to a solid support, such as a nickel-resin in the case of a His-tagged protein. Also contemplated by the invention are tags or other modifications that may be added to a protein post-synthetically. For example, a peptide can be biotinylated for affinity purification and immobilization using avidin or streptavidin reagents.

Thus, in one aspect, the MBD protein-mediated gene of the present invention is a recombinant, chimeric or fusion gene, expressed in vitro or in vivo. The nucleic acid encoding the MBD protein-mediated gene may be incorporated into an expression vector, which may be, for example, a self-replicating extrachromosomal vector, a vector which integrates into a host genome, or a linear nucleic acid that may or may not self-replicate. Detailed descriptions of methods for (i) the construction of promoter/reporter constructs, (ii) the assay of promoter function after transient transfection, and (ii) the quantitative detection of promoter mRNA by RT-PCR is well described in the art.

MBD2 selectively binds the GSTP1 CpG island when it is methylated, and siRNA-mediated reduction in MBD2 levels activates GSTP1 expression despite CpG island hypermethylation (see the Examples). Similarly, cells from Mbd2$^{-/-}$ mice are unable to repress transcription from exogenously hypermethylated promoters in transient transfection assays. Also, Apc$^{Min/+}$ Mbd2$^{-/-}$ mice develop far fewer intestinal adenomas, and survive longer, than do Apc$^{Min/+}$ Mbd2$^{+/-}$ or ApC$^{Min/+}$ Mbd2$^{+/+}$ mice. As for toxicity, other than a maternal behavior defect, the Mbd2$^{-/-}$ mice appear fairly unremarkable, and have maintained nominal gene imprinting, repression of endogeneous retroviral sequences, and no obvious ectopic gene expression. In contrast, Dnmt1$^{-/-}$, Dnmt3a$^{-/-}$ and Dnmt3b$^{-/-}$ mice are not viable. These observations show that MBD2-targeted drugs are able to reactivate "silenced" genes in cancer cells, or in pre-cancerous lesions, with a significant margin of safety.

Prevention and treatment of cancer using methods of the present invention applies to all cancers associated with epigenetic gene "silencing" due to gene hypermethylation. The terms "cell proliferative disorder" or "cellular proliferative disorder" refer to any disorder in which the proliferative capabilities of the affected cells is different from the normal proliferative capabilities of unaffected cells. An example of a cell proliferative disorder is neoplasia. Malignant cells (i.e., cancer) develop as a result of a multistep process. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the spread of a malignant tumor from its sight of origin. Cancer cells may metastasize through the bloodstream, through the lymphatic system, across body cavities, or any combination thereof. The term "cancerous cell" as provided herein, includes a cell afflicted by any one of the cancerous conditions provided herein. Accordingly, types of cancer can include, but are not limited to, colorectal cancer, esophageal cancer, stomach cancer, leukemia/lymphoma, lung cancer, prostate cancer, uterine cancer, breast cancer, skin cancer, endocrine cancer, urinary cancer, pancreatic cancer, other gastrointestinal cancer, ovarian cancer, cervical cancer, head cancer, neck cancer, kidney cancer, liver cancer, bladder cancer, breast cancer or adenomas.

A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is noncancerous, e.g. its cells do not proliferate or invade surrounding tissues. The term "malignant" refers to a tumor that is metastastic or no longer under normal cellular growth control.

As used herein, the term "ameliorating" or "treating" means that the clinical signs and/or the symptoms associated with the cancer or disease, such as sickle cell anemia, are lessened as a result of the actions performed. The signs or symptoms to be monitored will be characteristic of a particular cancer or melanoma and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

In one embodiment, the invention provides a method of reactivating a silenced gene having CpG island hypermethylation. The method includes contacting a cell with an agent that modulates methyl-binding domain (MBD) protein-mediated transcriptional repression, thereby increasing transcription of the silenced gene. In one aspect, the agent is an inhibitor of the interaction of a methyl-binding domain (MBD) protein with methylated genomic DNA.

The agent can be any agent identified by the present invention. In one example, the agent is a chemical compound. In another example, the agent is a chemical compound selected from those shown in Table 2.

In one aspect, the method may be applied to any hypermethylated gene. For example, the gene is selected from GSTP1, APC, HIC-1, RASSF1A, PTGS-2, EDNRB, MDR-1, ESR1, TIMP3, CDKN2A, CDKN2B, MLH1, MGMT, DAPK1, CDH1, ARF, IGF2, H19, p57/KIP2, KvLQT1, TSSC3, TSSC5, or ASCL2. In one example the gene is GSTP1.

Reactivation of the silenced gene can be performed with cells in a subject. In one aspect, the method further includes administering the agent to a subject having a disease associated with an epigenetically silenced gene. In one example the disease is cancer or sickle cell anemia.

In another embodiment, the present invention provides a method of preventing or treating cancer associated with CpG island hypermethylation of a gene in a subject. The method includes administering to a subject an agent that modulates methyl-binding domain (MBD) protein-mediated transcriptional repression, thereby increasing transcription of the gene and thereby preventing or treating the cancer. As previously discussed, it is well known in the art that hypermethylation of a number of genes is linked to cancer. As such, one aspect of the present invention, includes increasing transcription of any of such genes that are transcriptionally repressed due entirely, or in part, of one or more MBD proteins. In one aspect, the gene is selected from GSTP1, APC, HIC-1, RASSF1A, PTGS-2, EDNRB, MDR-1, ESR1, TIMP3, CDKN2A, CDKN2B, MLH1, MGMT, DAPK1, CDH1, ARF, IGF2, H19, p57/KIP2, KvLQT1, TSSC3, TSSC5, or ASCL2. In one example the gene is GSTP1. In another example, the MBD protein is MBD2 or MeCP2. However, the MBD protein can be any MBD protein that acts to mediate transcription of a "silenced" gene.

In any of the methods of the present invention, the agent may be an inhibitor of the interaction of an MBD protein with methylated genomic DNA. As such, the agent may interact directly with an MBD protein to inhibit or block binding or interaction of the protein with methylated DNA. For example, the agent may interact directly with MBD2, with $^{5-m}$CpG-containing DNA, or both, to prevent MBD2 from binding to $^{5-m}$CpG-containing GSTP1 promoter sequences. Alternatively, the agent may act indirectly through other proteins, such as binding to DNMTs or other proteins, resulting in inhibition of the interaction of an MBD protein with methylated genomic DNA. For example, the agent may target some other component of the MBD2 repression pathway.

While the term agent is broadly defined above, in one aspect, the agent utilized by any of the methods of the invention is a chemical compound. Exemplary chemical compounds useful for practicing any method of the present invention are shown in Table 2.

The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The agent can be administered in any way typical of an agent used to treat the particular type of cancer, or under conditions that facilitate contact of the agent with the target tumor cells and, if appropriate, entry into the cells. Entry of a polynucleotide agent into a cell, for example, can be facilitated by incorporating the polynucleotide into a viral vector that can infect the cells. If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell. Generally, an agent is formulated in a composition (e.g., a pharmaceutical composition) suitable for administration to the subject.

In one aspect, the agent may be combined with known chemotherapeutic agents, including but not limited to, Aclacinomycins, Actinomycins, Adriamycins, Ancitabines, Anthramycins, Azacitidines, Azaserines, 6-Azauridines, Bisantrenes, Bleomycins, Cactinomycins, Carmofurs, Carmustines, Carubicins, Carzinophilins, Chromomycins, Cisplatins, Cladribines, Cytarabines, Dactinomycins, Daunorubicins, Denopterins, 6-Diazo-5-Oxo-L-Norleucines, Doxifluridines, Doxorubicins, Edatrexates, Emitefurs, Enocitabines, Fepirubicins, Fludarabines, Fluorouracils, Gemcitabines, Idarubicins, Loxuridines, Menogarils, 6-Mercaptopurines, Methotrexates, Mithramycins, Mitomycins, Mycophenolic Acids, Nogalamycins, Olivomycines, Peplomycins, Pirarubicins, Piritrexims, Plicamycins, Porfiromycins, Pteropterins, Puromycins, Retinoic Acids, Streptonigrins, Streptozocins, Tagafurs, Tamoxifens, Thiamiprines, Thioguanines, Triamcinolones, Trimetrexates, Tubercidins, Vinblastines, Vincristines, Zinostatins, and Zorubicins.

In addition to treatment and prevention of cancer, methods of the present invention contemplate treatment of sickle cell anemia. Sickle cell anemia is caused by a point mutation in the beta-globin gene (HBb). Dimers of this mutant form of HBb multimerize with dimers of alpha-globin (Hba) to make sickle hemoglobin (HBs). HBs is prone to polymerization, causing sickling of red blood cells, and subsequent aberrant interactions between the sickled red blood cells, immune cells, and endothelial cells that result in a complex spectrum of disease manifestations.

One approach for the treatment of sickle cell anemia has been to prevent the polymerization of HBs by inducing expression of gamma-globin, a component of the fetal form of hemoglobin that is normally silenced in adult tissues by DNA methylation and binding of MBD2. By this approach, gamma-globin will compete with the mutant form of beta-globin to form fetal hemoglobin (HBf) instead of HBs. The resulting decrease in the concentration of HBs will prevent formation of the HBs polymers, as well as the downstream complications. Hydroxyurea is the most commonly used therapy for re-expression of beta-globin and/or interruption of the HBs polymerization process. However, the exact mechanism of hydroxyurea is not known, and may have many off target effects limiting potency and therapeutic window. Other investigational drugs include DNA methyltransferase nucleoside-analog inhibitors and histone-deacetylase inhibitors. Such drugs have the disadvantages discussed in previous sections of this report. MBD2 represents a target for treatment of sickle cell disease since it is apparently required for maintaining the silencing of gamma-globin. MBD2 inhibitors reported in the present invention, for example, some of which are shown in Table 2, can be efficacious in the reactivation of gamma-globin, and useful as agents in the treatment of sickle cell disease.

Accordingly, in one embodiment the invention provides a method of preventing or treating sickle cell anemia in a subject. The method includes administering to the subject an agent that modulates methyl-binding domain (MBD) protein-mediated transcriptional repression, thereby preventing or treating the sickle cell anemia. For example, the agent increases transcription of the gamma-globulin gene. In one aspect, the MBD protein is MBD2 or MeCP2. In another aspect, the agent is an inhibitor of the interaction of a methyl-binding domain (MBD) protein with methylated genomic DNA. In another aspect, the agent is a chemical compound. In another aspect, the agent is a chemical compound selected from those shown in Table 2.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

CpG Island Hypermethylation in the Pathogenesis of Human Prostate Cancer

Figure 2:
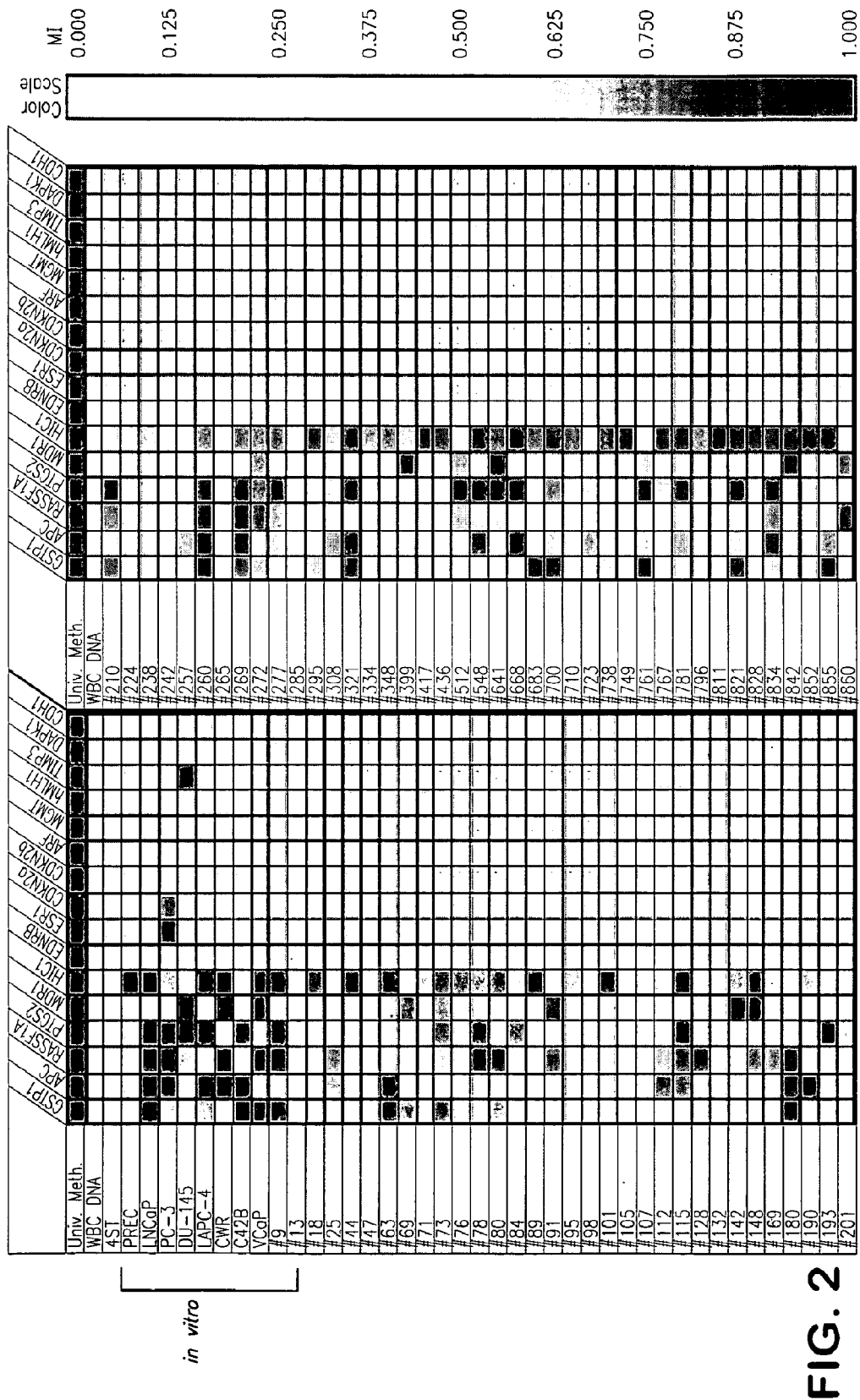
FIG. 2 is a graphical representation showing a CpG island methylation index for normal prostate cells and prostate cancer cell lines in vitro, and for localized prostate cancer cases in vivo, sampling GSTP1, APC, HIC-1, RASSF1A, PTGS-2, EDNRB, MDR1, ESR1, TIMP3, CDKN2A, CDKN2B, MLH1, MGMT, DAPK1, CDH1 and ARF, using quantitative MS-PCR methods.
Figure 3:
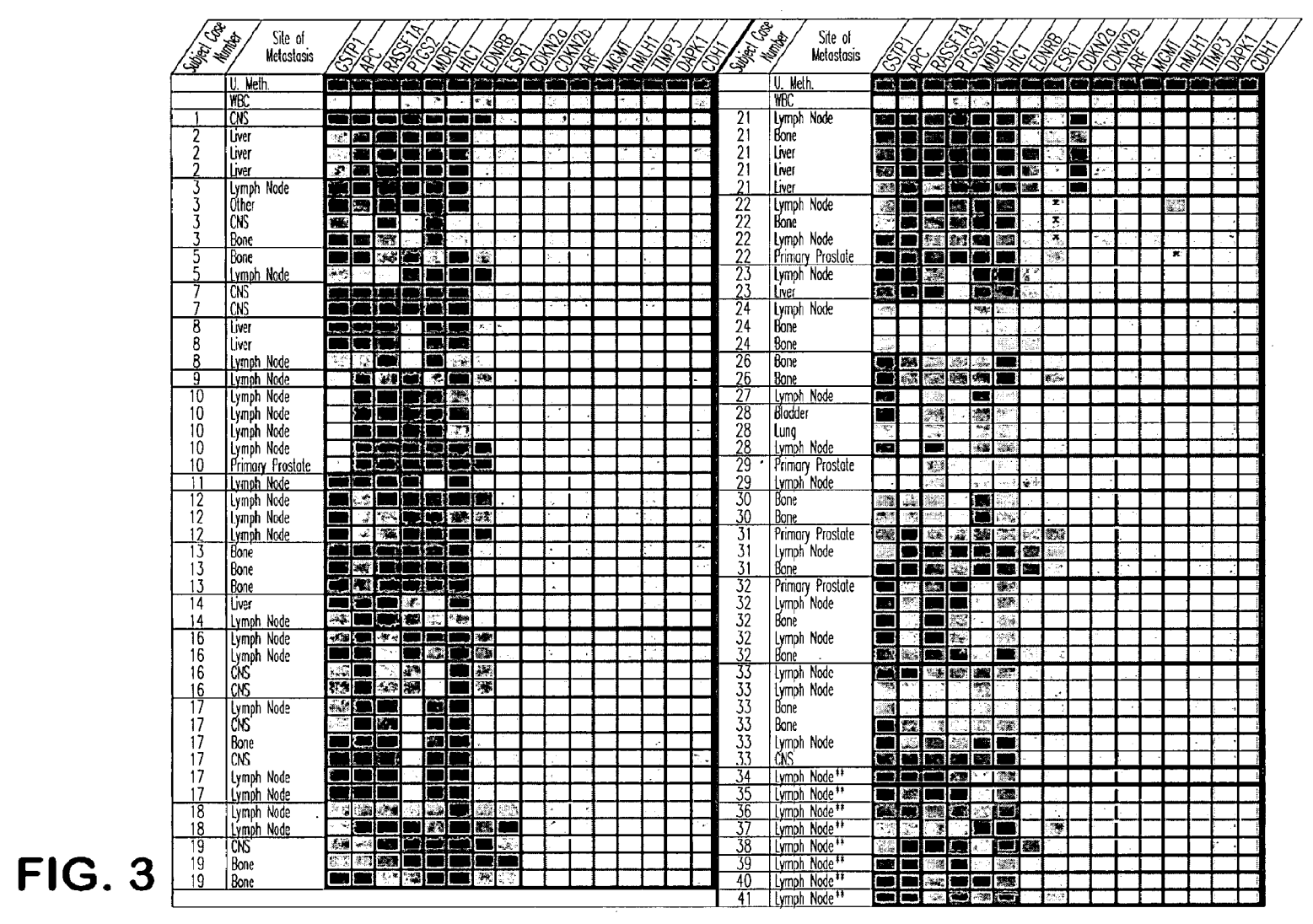
Figure 4:
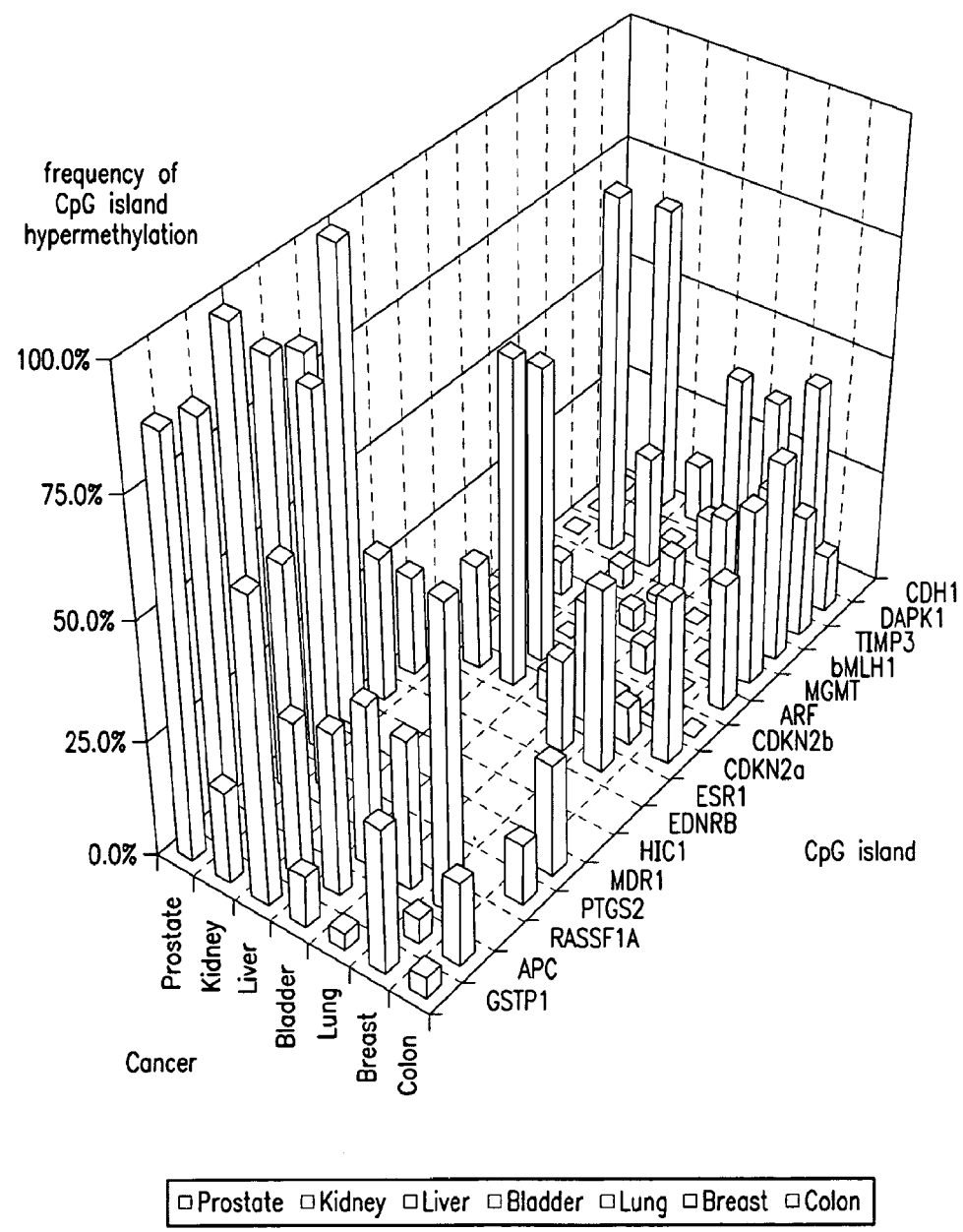
FIG. 4 is a graphical representation showing distinct patterns of CpG island hypermethylation in human cancers.
Figure 5:
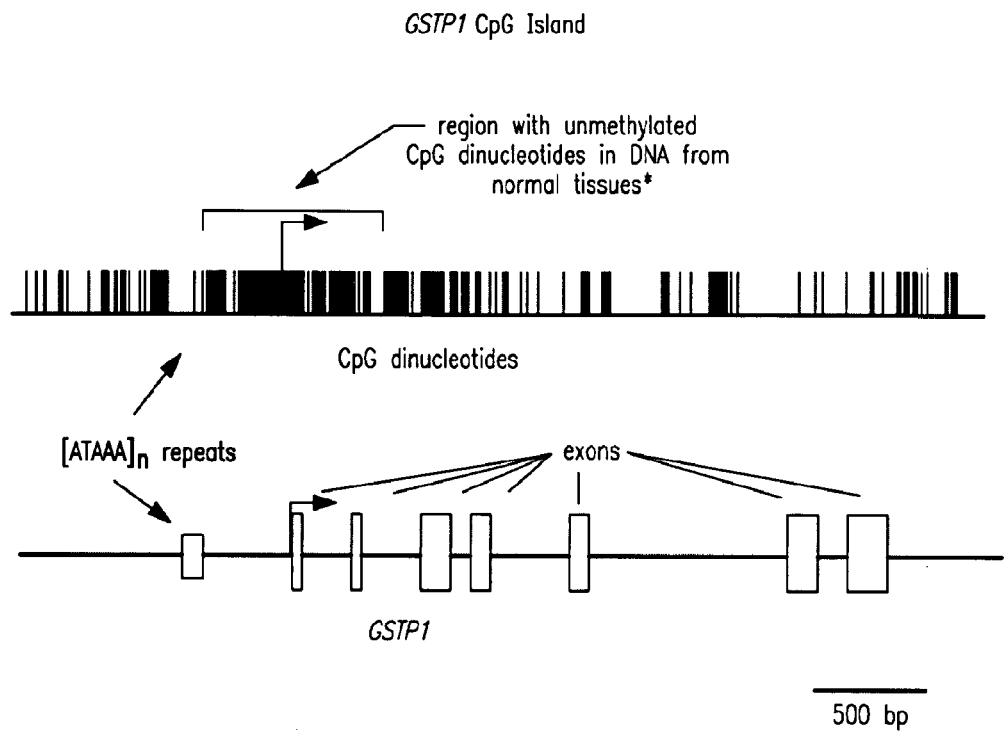
FIG. 5 is a pictorial diagram illustrating the GSTP1 CpG island region encompassing the transcriptional promoter unmethylated in all normal tissues and extensively methylated in cancers, such as prostate, breast, and liver cancers.
Figure 6:
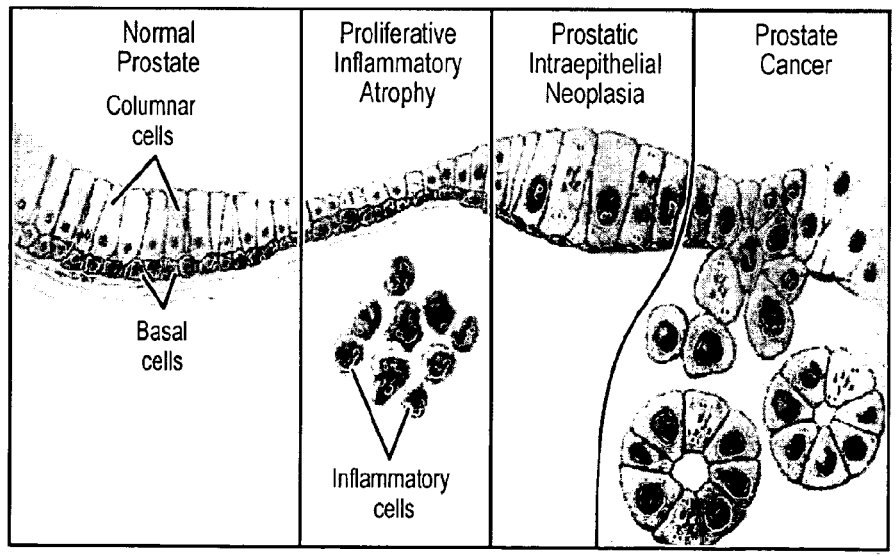
FIG. 6 is a pictorial diagram illustrating histopathogenesis of prostate cancer, from normal prostate, to proliferative inflammatory atrophy (PIA), to prostatic intraepithelial neoplasia (PIN), to prostate cancer.
Figure 7:
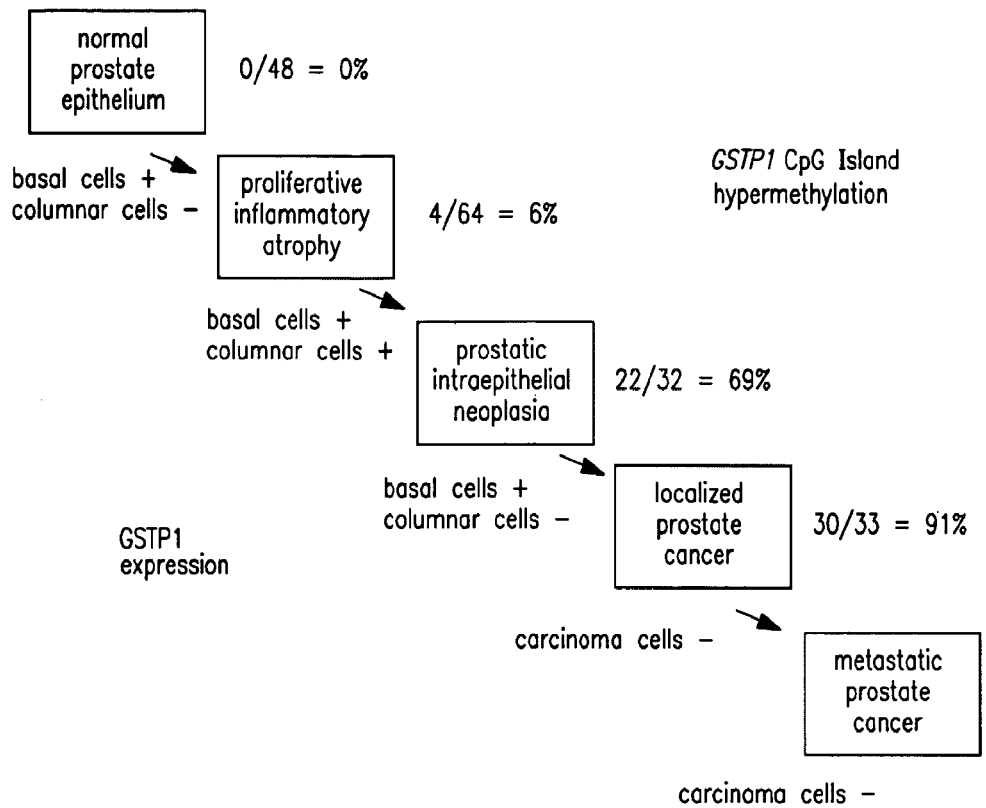
FIG. 7 is a pictorial diagram illustrating GSTP1 Cp-G island hypermethylation appearing early during, prostatic carcinogenesis, arising in PIA and PIN lesions that are precursors to prostate cancer.

Using quantitative DNA methylation-specific PCR (MS-PCR), the presence or absence of CpG island hypermethylation at GSTP1, APC, HIC-1, RASSF1A, PTGS-2, EDNRB, MDR1, ESR1, TIMP3, CDKN2A, CDKN2B, MLH1, MGMT, DAPK1, CDH1, and ARF, was assessed using genomic DNA from various human prostate cancer cell lines cultivated in vitro, as well as from primary and metastatic prostate cancer cases (FIGS. 2-4). Next, when laser capture micro-dissection was used to selectively isolate epithelial cells from normal prostate, from proliferative inflammatory atrophy (PIA) lesions, from prostatic intraepithelial neoplasia (PIN) lesions, and from prostatic carcinomas, analysis of genomic DNA by MS-PCR revealed the appearance of GSTP1 CpG island hypermethylation in prostate cancer precursors (PIA and PIN) as well as prostate cancers (FIGS. 5-7).

Figure 8:
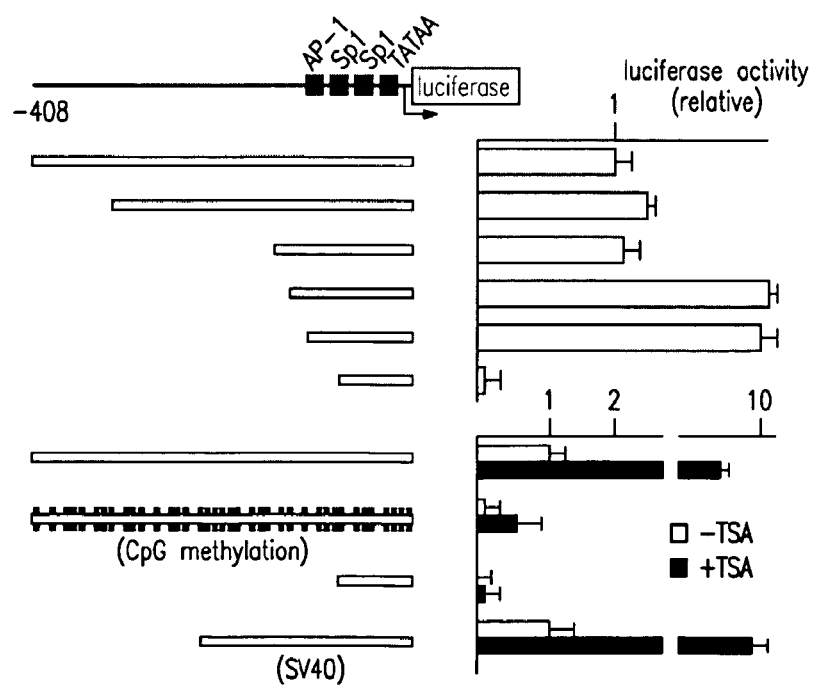
FIG. 8 is a pictorial diagram illustrating CpG island hypermethylation repression of the activity of GSTP1 promoters upon transfection into MCF-7 breast cancer cells.
Figure 9A:
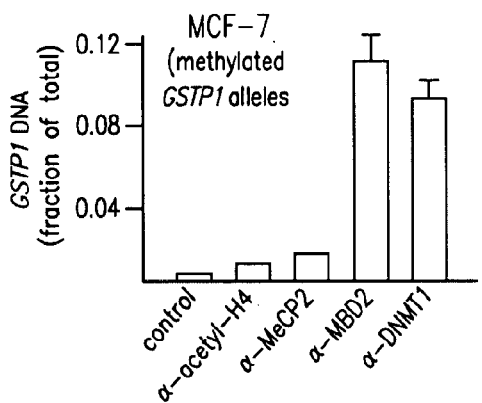
FIGS. 9A-9C are graphical representations showing chromatin immunoprecipitation (ChIP) analysis of MBD proteins at the GSTP1 promoter in MCF-7 cells (A), with "silenced" GSTP1 alleles, and in MCF-7/ADR cells (B), with active GSTP1 alleles, reveals selective association of MBD2 with "silenced" GSTP1 alleles. In contrast, at "silenced" MDR1 alleles in MCF-7 cells (C), both MBD and MeCP2 are present.
Figure 9C:
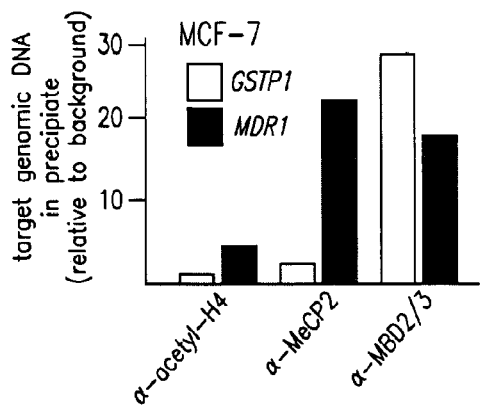
Figure 9B:
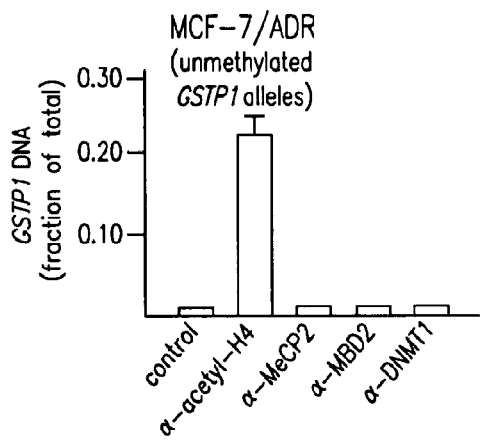
Figure 10:
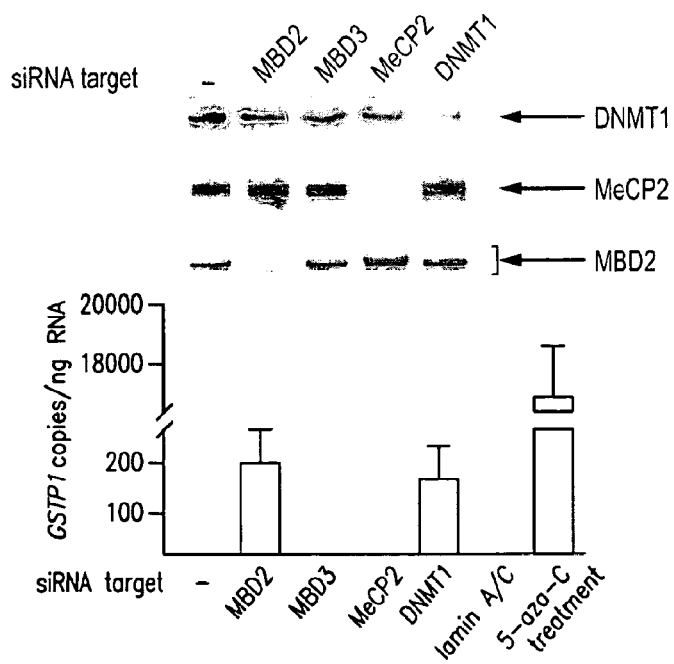
FIG. 10 is a graphical representation and pictorial diagram showing siRNA targeting mRNA encoding MBD2, but not MeCP2 triggers reactivation of GSTP1 expression in MCF-7 cells as efficiently as siRNA targeting DNMT1 mRNA.

MBD2 mediates repression of GSTP1 genes with hypermethylated CpG islands in MCF-7 breast cancer cells. GSTP1, encoding the π-class GST, has not only been reported to be the target of somatic CpG island hypermethylation in >90% of prostate cancers, but also in >80% of liver cancers, and in >30% of breast cancers. For each of these cancer cell types, GSTP1 CpG island hypermethylation has been shown to be responsible for absence of GSTP1 expression (FIG. 8). The evidence that the MBD family protein MBD2 binds to hypermethylated GSTP1 CpG island sequences to prevent GSTP1 transcription is as follows: (i) MBD2 (along with DNMT1), but not the MBD family protein MeCP2, was detected bound to GSTP1 promoter sequences, using chromatin immunoprecipitation (ChIP) analyses, in MCF-7 breast cancer cells only when the GSTP1 CpG island was hypermethylated (FIG. 9), and (ii) treatment of MCF-7 cells with siRNA targeting MBD2 mRNA, but not with siRNA targeting MeCP2 or lamin A mRA, activated transcription from hypermethylated GSTP1 promoters (FIG. 10).

MBD2-mediated repression of transcription from hypermethylated GSTP1 promoters can be recapitulated in transient transfection assays. When GSTP1 promoter sequences were exogenously methylated by treatment with the CpG methyltransferase SssI, and transfected into Hep3B liver cancer cells, MBD2, but not MeCP2, was attached to the promoter, as detected using ChIP analysis, and reporter expression was repressed in a manner that could be alleviated via siRNA "knockdown" of MBD2, but not MeCP2, levels (FIG. 11).

EXAMPLE 2

Discovery of Small Molecule MBD Antagonists

To identify and characterize small molecules that antagonize MBD2-mediated repression of transcription from genes with hypermethylated CpG islands, three objectives were pursued.

A 2-stage "high-throughput" screening strategy identified "lead" compounds from a chemical diversity library (a ChemBridge collection of n=10,000 compounds). A 2-stage screening strategy exploited the dependence of transcriptional repression associated with GSTP1 CpG island hypermethylation on MBD2, to identify MBD2 pathway inhibitors (see Example 1). siRNA-triggered "knock-down" of MBD2 protein levels in human cancer cells is known to alleviate repression of hypermethylated GSTP1 promoter sequences both for transfected promoter/reporter constructs (FIG. 11), the basis for the first screening stage, and for native GSTP1 alleles in situ (FIG. 10), the basis of the second screening stage. The integrated screening strategy involved: stage 1, a readily scalable cell-based screening approach focused on transfected GSTP1 promoter/reporter constructs, and stage 2, a confirmatory cell-based assay monitored reactivation of "silenced" GSTP1 alleles in situ via quantitative reverse transcriptase-PCR (RT-PCR) measurements of GSTP1 mRNA levels. 10,000 compounds from the ChemBridge PHARMCOPHORE™ collection were screened.

A 2-stage screening strategy for MBD2 transcription repression pathway antagonists: stage 1. The first stage of the screening strategy for MBD2 hypermethylated CpG island transcriptional repression pathway inhibitors features the use of two GSTP1 promoter/*luciferase* reporter constructs: one treated with SssI CpG methyltransferase controlling Firefly *luciferase*; the other left free of $^{5-m}$CpG controlling *Renilla luciferase*. After simultaneous transfection into cancer cells and exposure to chemical library compounds in multi-well plates, several patterns of transcription induction were distinguished: (i) compounds that induce both hypermethylated and unmethylated promoter sequences, (ii) compounds that are incapable of augmenting expression from either promoter, (ii) compounds that selectively activate unmethylated promoter sequences, and (iv) compounds, defined as "hits," that selectively increase expression from hypermethylated promoter sequences (FIG. 12).

Figure 13:
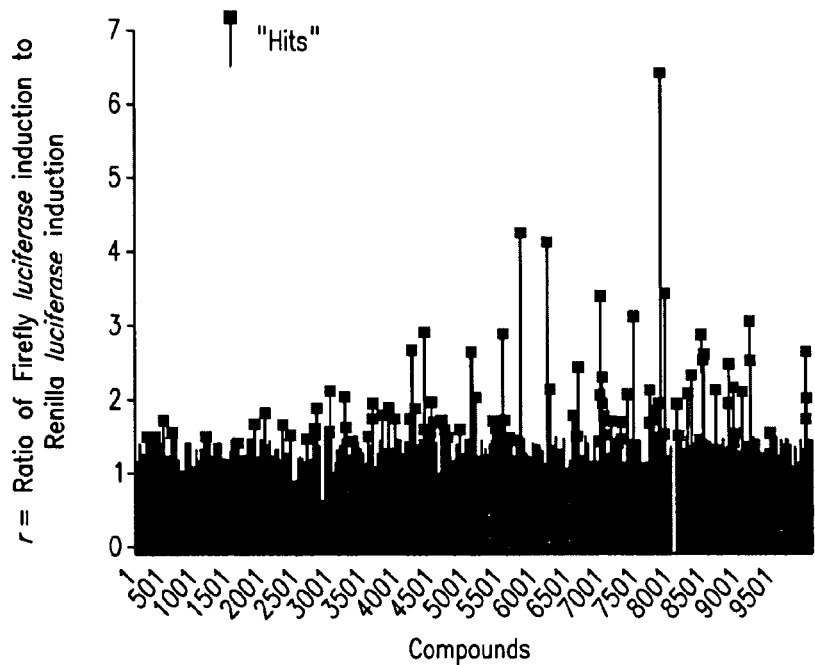
FIG. 13 is a graphical representation showing "hits" from stage 1 screening of 10,000 ChemBridge PHARMCOPH-ORE™ compounds (r>1.5 with Firefly *luciferase* induction>1) that selectively activate expression from transfected GSTP 1 promoters with hypermethylated CpG islands.

In preliminary experiments, siRNA targeting MBD2 mRNA ("knocking-down" MBD2 polypeptide levels) gave a "hit" pattern of promoter induction (FIG. 11). To adjust for short-term toxicity to the cancer cells, simultaneous screening of the chemical library compounds for rapid cancer cell killing via an XTT assay was performed. Using this strategy, 10,000 ChemBridge PHARMCOPHORE™ compounds, at a concentration of 10 μM, were screened for MBD pathway antagonism using MCF-7 cells in a 96-well cell culture format (FIG. 13). The performance characteristics of the screening assay incorporated stage 1 screening results (restricted to non-toxic compounds by XTT assay) were displayed as the ratio (r) of Firefly *luciferase* induction to *Renilla luciferase* induction ($r=F_f/F_u \div R_f/R_u$ where $F_f$=Firefly *luciferase* activity in a compound-treated well, $F_u$=Firefly *luciferase* activity in a control well, $R_f$=*Renilla luciferase* activity in a compound-treated well, and $R_u$=*Renilla luciferase* activity in a control well), a "cut-off" value of r>1.5 with $F_f/F_u$>1.0 provided a 1.42% "hit" rate.

Figure 14:
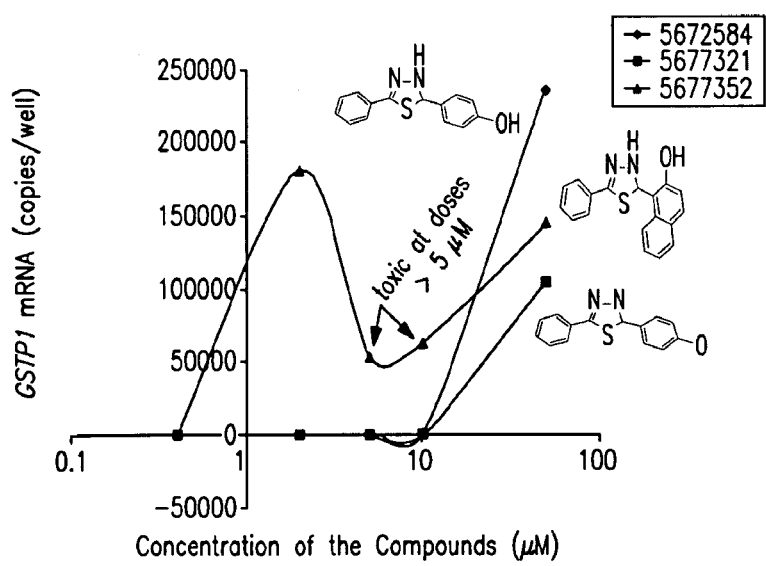
FIG. 14 is a graphical representation illustrating the stage 2 screening assay for activation of GSTP1 mRNA expression in MCF-7 cells with hypermethylated GSTP1 CpG islands. Dose-response analysis of 3 similar "hit" compounds evidence structure-activity relationships.
Figure 15:
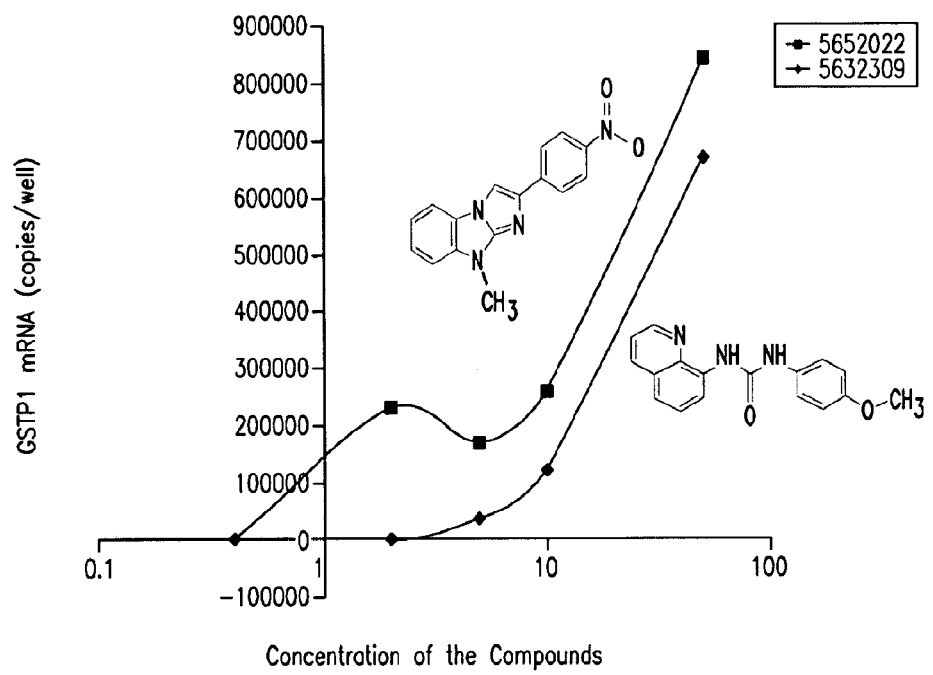
FIG. 15 is a graphical representation showing the dose-response characteristics of 2 "hit" compounds using the stage 2 assay for activation of GSTP1 expression in MCF-7 cells.
Figure 16:
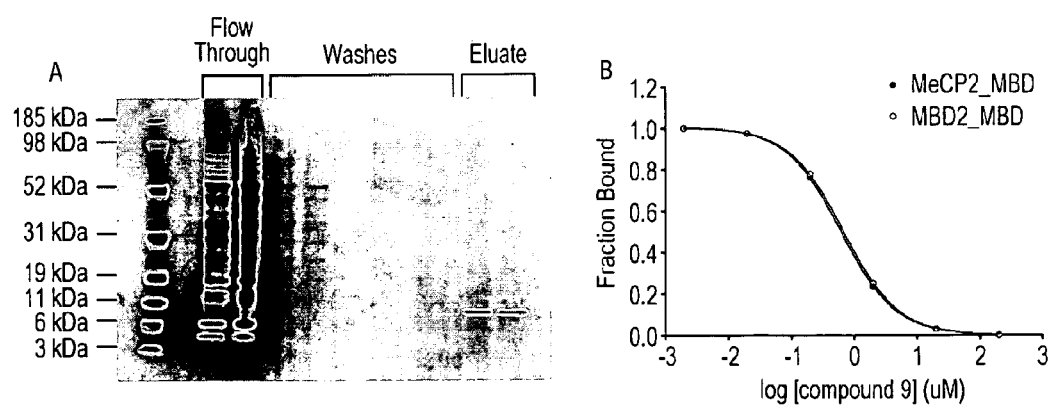
FIG. 16A is a pictorial representation showing baculovirus-mediated expression of C-terminal His6-tagged MBD in Sf9 insect cells and purification by Ni-NTA beads. The eluate contained purified 9.8 kDa MBD-His6.
FIG. 16B is a graphical representation showing inhibition of MBD2, MeCP2_MBD binding to $^{5mC}$-containing DNA.

The second stage of the screening strategy involved subjecting "hits" identified in stage 1 to a "medium-throughput" assay testing whether "hit" compounds could increase GSTP1 mRNA expression from cells with hypermethylated GSTP1 CpG islands. For this assay approach, quantitative RT-PCR for detection of GSTP1 mRA was adapted to 96-well plate format. As with the stage 1 screening assay, the stage 2 assay correctly identified siRNA targeting MBD2 mRNA as a "lead" (FIG. 10). The performance characteristics of this screening activity also appear reasonable: of 142 "hits" from stage 1 screening of 10,000 ChemBridge PHARMCOPH-ORE™ compounds, 24 (1.69% of "hits" and 0.24% of total compounds screened) induced GSTP1 mRNA expression in MCF-7 cancer cells. For each "lead" compound, the stage 2 screening assay was used to assess dose-response properties, providing potency ($EC_{50}$)) and efficacy (maximal GSTP1 mRNA induction) data (FIGS. 14-15).

Detailed descriptions of methods have been described for (i) the construction of hypermethylated GSTP1 promoter/reporter constructs, (ii) the assay of GSTP1 promoter function after transient transfection, and (ii) the quantitative detection of GSTP1 mRNA by RT-PCR.

Construction of GSTP1 promoter-*Renilla luciferase* and pGSTP1-Firefly *luciferase* and treatment of plasmids with SssI CpG methylase. GSTP1 promoter sequences (GenBan positions −408 to +36), recovered from pGSTP1-CAT via excision using HindIII and SalI and cloning in pBluescript™ (Stratagene), were introduced into pGL3-Basic™ (Promega), a promoter-less vector containing Firefly *luciferase* cDNA, and into pRL-Null™ (Promega), a promoter-less vector containing *Renilla luciferase* cDNA. Methylation of GSTP1 CpG island sequences in promoter/reporter plasmid constructs was accomplished using the CpG methylase SssI (New England BioLabs). The reaction mixtures featured 200 μg plasmid DNA, 160 μM S-adenosylmethionine, and 200,000 units SssI in 50 mM NaCl, 10 mM tris-HCl, 10 mM $MgCl_2$, and 1 mM DTT; the mixture was incubated at 37° C. for 60 minutes.

Assessment of GSTP1 promoter activity. Growing MCF-7 cells were simultaneously transfected with SssI-treated pGSTP1 promoter-Firefly *luciferase* and non-SssI-treated pGSTP1 promoter-*Renilla luciferase* constructs as described previously, seeded into 96-well plates, and exposed to various small molecule inhibitor candidates (at 10 μM) in complete growth medium. To assess reporter gene expression, the transfected cells were lysed 48 hours after small molecule inhibitor exposure and then assayed for *luciferase* activity using the DUAL-*LUCIFERASE*® REPORTER ASSAY SYSTEM from Promega.

The ChemBridge PHARMCOPHORE™ library of chemical compounds. The PHARMCOPHORE™ diverse chemical library from ChemBridge contains 100,000 compounds, 10,000 of which were used in the "high-throughput" screening assay of the present invention. Quality control testing at ChemBridge reveals >90% purity by NMR for 94% of library compounds. Also, sufficient quantities of "hit" compounds are available at ChemBridge for re-supply to permit characterization studies. At the Johns Hopkins University School of Medicine, access to the ChemBridge PHARMCOPHORE™ compounds is facilitated by the High Throughput Biology (HiT) Center. The HiT Center serves as a Core Resource at the School of Medicine to provide access to chemical diversity libraries, robotic technologies for expanding the scope of screening studies, and consultation for the design of screening assays. The initial 10,000 ChemBridge PHARMCOPH-ORE™ compounds used were obtained from the HiT Center.

XTT assay for cell viability. MCF-7 cells, 24 hours after seeding into 96-well cell culture dishes at $5 \times 10^3$ cells/well, were exposed to ChemBridge PHARMCOPHORE™ library compounds at a concentration of 10 μM. 48 hours later, 50 μL XTT labeling mixture (Roche Molecular Biochemicals) was added to each cell culture well. After 4 hours incubation at 37° C., cell viability was assessed by monitoring absorbance ($A_{492nm}-A_{690nm}$), which was measured for each well and compared to the mean and standard deviation for each plate. Compounds are designated as "toxic" if the absorbance is less than two standard deviations below the plate mean.

Characterization of "lead" compounds identified by the "high-throughput" screen. "Lead" compounds identified by the 2-stage screening approach activated expression from hypermethylated GSTP1 CpG island alleles. These "lead" compounds accomplish this feat by interacting directly with MBD2, with $^{5-m}$CpG-containing DNA, or both, to prevent MBD2 from binding to $^{5-m}$CpG-containing GSTP1 promoter sequences. Alternatively, the "lead" compounds act indirectly by targeting some other component of the MBD2 repression pathway. Both direct and indirect MBD2 pathway inhibitors are appropriate for further attention. In addition, some "lead" compounds might reactivate expression from hypermethylated GSTP1 CpG island alleles via a mechanism independent of MBD2, such as by inhibition of DNMTs. As described above, the 2-stage screening assay employed would be unlikely to identify compounds that solely inhibit DNMTs as "leads." However, like MBD2, DNMTs recognize and bind DNA sequences containing $^{5-m}$CpG. As a consequence, some "lead" compounds might act both to interfere with MBD2 binding to $^{5-m}$CpG containing DNA and to inhibit DNMTs.

To determine if the "lead" compounds directly interfere with MBD2 binding to $^{5-m}$ CpG containing DNA, each "lead" compound is tested for its ability to inhibit such binding using a DNA-protein binding assay. For this assay, a biotinylated and methylated oligonucleotide substrate is bound to a neutravidin-coated high binding capacity 96-well plate. His-tagged MBD2_MBD or MeCP2_MBD binds to the methylated oligonucleotide. An Anti-His-HRP conjugated antibody is used to detect bound protein. Introducing the "lead" compounds into the reaction mix at various concentrations provides a MBD2_MBD-DNA binding curve from which an $IC_{50}$ is derived.

To ascertain whether any of the "lead" compounds inhibit DNMTs, the compounds are tested for ability to inhibit DNA methylation catalyzed by recombinant DNMT1, DNMT3a, and/or DNMT3b. The outputs of these experiments were $K_i$'s for each of the DNMT enzymes. When considered along with potency and efficacy data from the screening assays, the results of analyses of "lead" compounds for interference with MBD2 binding to $^{5-m}$ CpG-containing DNA, for direct binding to $^{5-m}$CpG-containing DNA, and for inhibition of DNMTs allow prioritization of "lead" compounds. Ideally, "lead" compounds that activate expression from GSTP1 alleles with CpG island hypermethylation at sub-μM concentrations, target MBD2 directly, and fail to inhibit DNMTs, are high-priority "lead" compounds.

Figure 17:
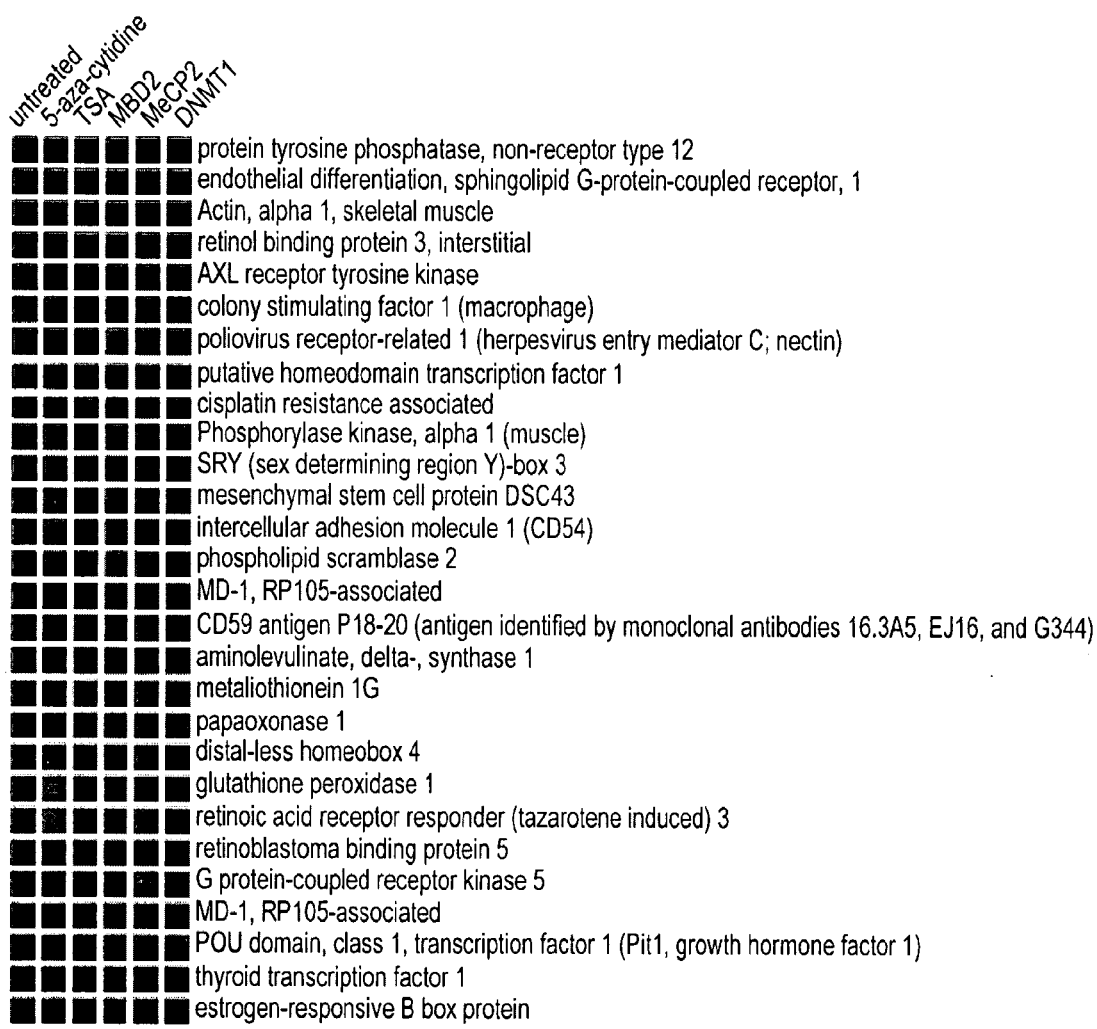
FIG. 17 is a pictorial representation showing cDNA microarray analysis of changes in patters of gene expression in MCG-7 cells accompanying treatment with 5-aza-C or trichostatin A, and associated with siRNA-mediated "knock-down" of MBD2, MeCP2, or DMNT1.

Finally, to further assess the "on-target" and "off-target" properties of high-priority "lead" compounds, the effects of such compounds on global gene expression profiles in cancer cells, in comparison to the effects of siRNA "knock-down" of MBD2 expression, is contemplated to be analyzed. Anticipating these analyses, the consequences of targeted MBD2 "knock-down," versus "knock-down" of MeCP2 and DNMT1, on gene expression in MCF-7 cells have been explored via transcriptome profiling (FIG. 17).

DNA binding assays using recombinant MBDs. To produce recombinant His6-tagged MBD polypeptides from human MBD2 (MBD2-MBD), MBD2-MBD cDNA was amplified from clone MGC-45084 (American Type Culture Collection), using PCR primers containing BamHI and EcoRI recognition sites (5'-GGATCCATGGAGAGCGG-GAAGAGGATGGA-3' (SEQ ID NO:1) and 5'-GAATTC-CATCTTTCCAGTTCTGAAGT-3' (SEQ ID NO:2)), and then introduced into pFBC6H, a modified pFastBac-1® baculovirus expression vector (Invitrogen), that had been linearized via cutting with EcoRI and XbaI. This pFB6H-MBD2 expression construct was used to transform DH10Bac™ E. coli competent cells (Invitrogen) to form an MBD2 expression bacmid via site-specific transposition. The MBD2 expression bacmid was then transfected into Sf9 insect cells for production of recombinant MBD2 baculovirus particles, which were used to infect Sf9 cells (1 MOI, 48 hours) to generate recombinant MBD2 protein. To recover recombinant MBD2 protein, the infected Sf9 cells were homogenized, using a Dounce homogenizer, in a buffer containing 20 mM HEPES, 25% glycerol, 0.42M NaCl, 1.5 mM MgCl$_2$, 0.2 mM EDTA, 0.5 mM PMSF, 0.5 μg/mL Leupeptin, and 0.5 mM DTT. After centrifugation in a microfuge, the soluble protein fraction, containing MBD2, was recovered. A similar approach was used for producing cloned recombinant MeCP2. For binding assays, biotinylated 45-bp oligonucleotide (Top Strand 5'-GA$^{5-m}$CGT$^{5-m}$CGTT$^{5-m}$CGTA$^{5-m}$CGCT$^{5-m}$CGTT$^{5-m}$CGACT$^{5-m}$CGTG$^{5-m}$CGA$^{5-m}$CG-GAT$^{5-m}$CGGATTG 3' (SEQ ID NO:20), Bottom Strand 5'-CAATCC$^{5-m}$GATC$^{5-m}$CGT$^{5-m}$CGCA$^{5-m}$CGAGT$^{5-m}$C-GAA$^{5-m}$CGAG$^{5-m}$CGTA$^{5-m}$CGAA$^{5-m}$CGA$^{5-m}$CGTC 3' (SEQ ID NO:3)) is combined with MBD2_MBD or MeCP2_MBD (0.25 μM) in binding buffer (10 mM NaCl, 1 mM EDTA, 25 mM Tris-HCl (pH 7.4). "Lead" compounds (diluted in DMSO) are added to each well at various concentrations and incubate in reaction mix for 1 hour at RT in a neutravidin-coated high binding capacity 96-well plate (Pierce, 15507). After washing wells twice with binding buffer, protein is incubated with Anti-His-HRP conjugated Ab (1:1000) (Qiagen, 34460) for 1 hour at RT. After washing four times with binding buffer and drying wells, TMB is added to each well followed by 1 N HCl, and $A_{450}$ is measured on a microplate reader. The $IC_{50}$ for each "lead" compound is derived from the DNA-protein binding curve.

DNMT assays using recombinant DNMT1, DNMT3a, and DNMT3b. To produce recombinant DNMT1, full-length DNMT1 cDNA was amplified in two segments by RT-PCR from human brain poly A+ RNA (BD Clontech). Amplification of the upstream segment was performed using the PCR primers (5'-CCTCTCTCCGTTTGGTACATCC-3' (SEQ ID NO:4) and 5'-CACAGGTGACCGTGCTTACAGT-3' (SEQ ID NO:5)), and amplification of the downstream segment was performed using the PCR primers (5'-AGCACAAACTGAC-CTGCTTCAG-3' (SEQ ID NO:6) and 5'-ATCAGTGCAT-GTTGGGGATTC-3' (SEQ ID NO:7)). The upstream and downstream segments were subcloned into the pCMVscript® vector (Stratagene), and assembled using an internal BstEII site that is common to both segments to create pCMVscript-DNMT1. PCR primers containing EcoRI and KpnI sites (5'-GAATTCCCGGCGCGTACCG-3' (SEQ ID NO:8) and 5'-GGTACCCTAGTCCTTAGCAGCTTCCTCCT-3' (SEQ ID NO:9)) were used to amplify the DNMT1 coding sequence from pCMVscript-DNMT1. The product was subcloned into pFB6H, a modified pFastBac-1® baculovirus expression vector (Invitrogen) that contains a 6× His tag (SEQ ID NO:21). This pFB6H-DNMT1 construct was used to transform DH10Bac™ E. coli competent cells (Invitrogen) to generate a recombinant expression bacmid via site-specific transposition. The DNMT1 expression bacmid was transfected into Sf9 insect cells to produce recombinant DNMT1 baculovirus particles, which were subsequently used to infect additional Sf9 cells (1 MOI, 48 hours) for protein production. Recombinant His$_{(6)}$-(SEQ ID NO:21)-DNMT1 was recovered by Ni$_2$+ affinity chromatography. After lysis in 50 mM Na$_2$HPO$_4$ pH 7.6, 10 mM imidazole, 500 mM NaCl, 1% Igepal CA-630, 10% glycerol, and 1× Complete™ Protease Inhibitor (Roche) by two freeze-thaw cycles, His$_{(6)}$-(SEQ ID NO:21)-DNMT1 was bound to Ni-NTA agarose (Qiagen) for 1.5 hours at 4° C. The supernatant was removed, and the beads were washed twice with 50 mM Na$_2$HPO$_4$ pH 7.6, 20 mM imidazole, 500 mM NaCl, 10% glycerol, and 1× Complete™ Protease Inhibitor to remove contaminating proteins. The beads were then washed twice with 50 mM Na$_2$HPO$_4$ pH 7.6, 10 mM NaCl, 10% glycerol, and 1× Complete™ Protease Inhibitor to remove excess salt. His$_{(6)}$-(SEQ ID NO:21)-DNMT1 was eluted from the Ni-NTA agarose by adding 50 mM Na$_2$HPO$_4$ pH 7.6, 250 mM imidazole, 10 mM NaCl, 10% glycerol, and 1× Complete™ Protease Inhibitor. Spin dialysis was used to concentrate the protein and exchange the buffer 50 mM Na$_2$HPO$_4$ pH 7.6, 10 mM NaCl, 1 mM EDTA, 1 mM DTT, 20% glycerol, and 1× Complete™ Protease Inhibitor. Protein concentration was determined using the BCA assay (Pierce). Recombinant DNMT1 was stored at −80° C. until further use.

His$_{(6)}$-(SEQ ID NO:21)-DNMT3a and His$_{(6)}$-(SEQ ID NO:21)-DNM3b2 were expressed and purified in Sf9 cells as described above with the following modifications. Full length DNMT3a cDNA was amplified from human testis Poly A+ RNA by RT-PCR with the primers (5'-GCTCAACACCGG-GATCTATGTT-3' (SEQ ID NO:10) and 5'-CTACCT-CAGTTTGCCCCCATGT-3' (SEQ ID NO:11)) and subcloned into pCR-BluntI-TOPO® vector (Invitrogen). PCR primers containing EcoRI and XbaI sites (5'-GAATTC-CCCGCCATGCCCTC-3' (SEQ ID NO:12) and 5'-TCTA-GATTACACACACGCAAATACTCCTTC-3' (SEQ ID NO:13)) were used to amplify the DNMT3a coding sequence from pCR-BluntII-TOPO-DNMT3a. The product was subcloned into pFB6H to create pFB6H-DNMT3a. Full length DNMT3b2 cDNA was amplified from human testis Poly A+ RNA by RT-PCR with the primers (5'-ATGAAGGGAGA-CACCAGGCA-3' (SEQ ID NO:14) and 5'-GGATGCCT-TCAGGAATCACAC-3' (SEQ ID NO:15)) and subcloned into pCR-BluntII-TOPO® vector (Invitrogen). PCR primers containing EcoRI and XbaI sites (5'-GAATTCAAGG-GAGACACCAGGCATCT-3' (SEQ ID NO:16) and 5'-TCTAGACTATTCACATGCAAAGTAGTCCTTCAG-3' (SEQ ID NO:17)) were used to amplify the DNMT3b2 coding sequence from pCR-BluntI-TOPO-DNMT3b2. The product was subcloned into pFB6H to create pFB6H-DNMT3b2.

Figure 18:
Figure 19:
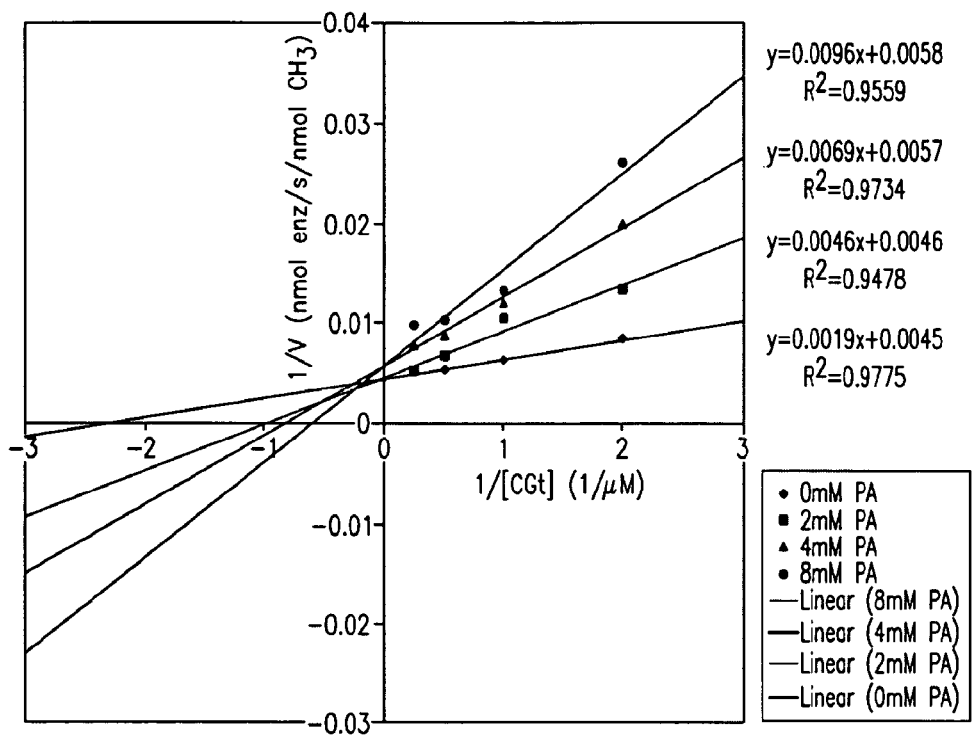
Figure 20:
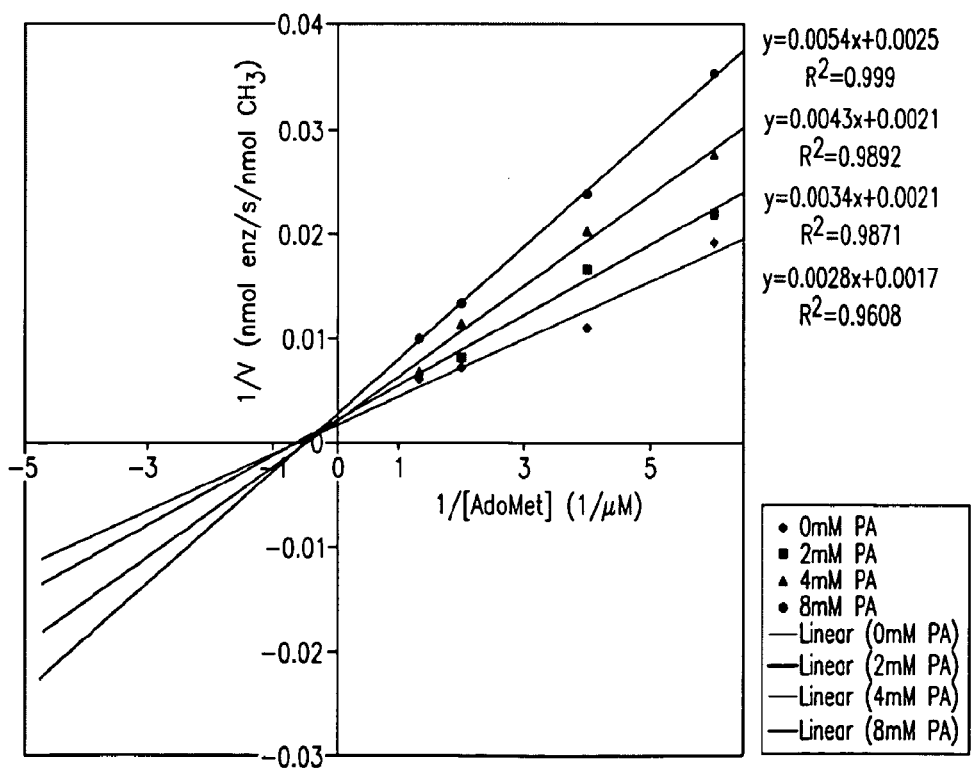
FIG. 20 is a graphical representation showing Lineweaver-Burk analysis of procainamide inhibition of DNMT3a FIG. 21 is a pictorial representation illustrating screening to identify high-priority "lead" compound MBD2 Pathway antagonists for evaluation in preclinical models.
Figure 21:
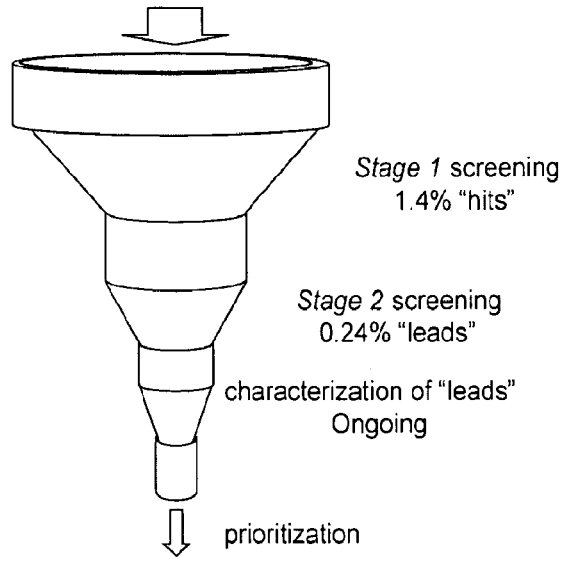
Figure 22:
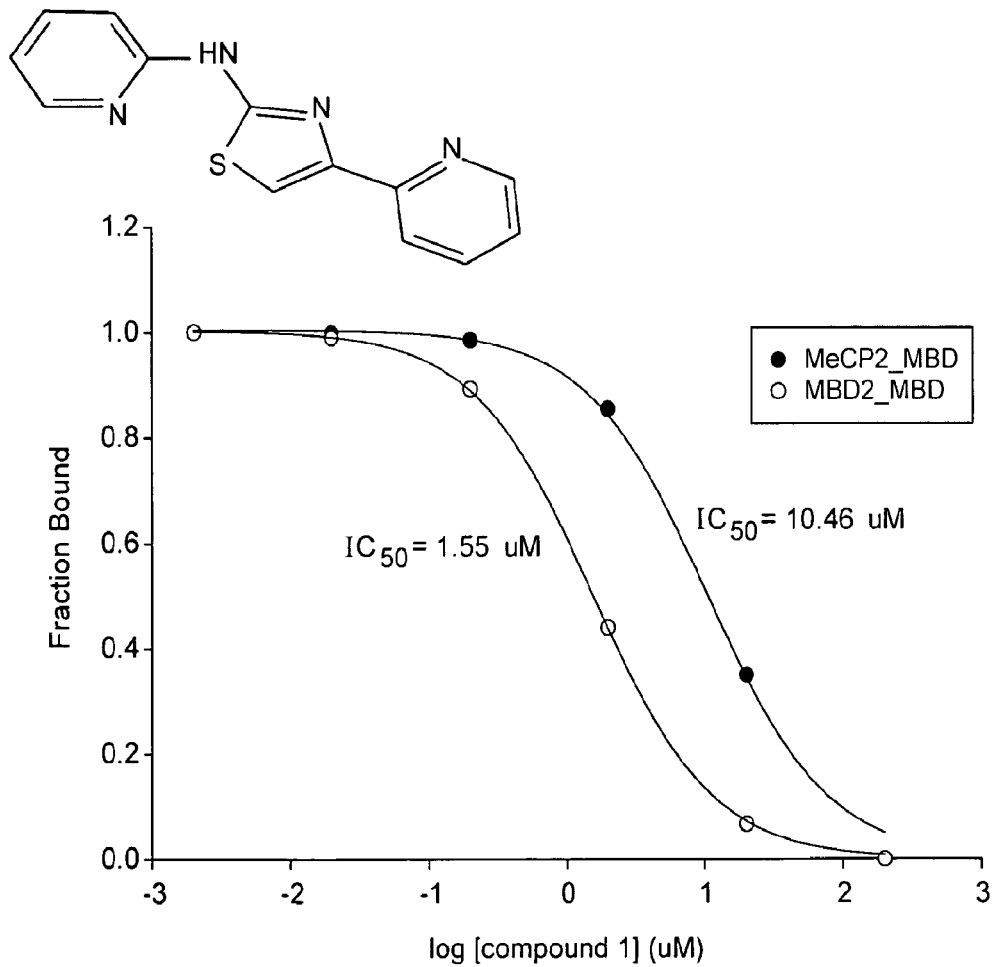
FIG. 22 is a graphical representation of the ability of a chemical compound to inhibit binding of the methyl-binding domain of MBD2 and MeCP2 to symmetrically methylated DNA oligonucleotides.
Figure 23:
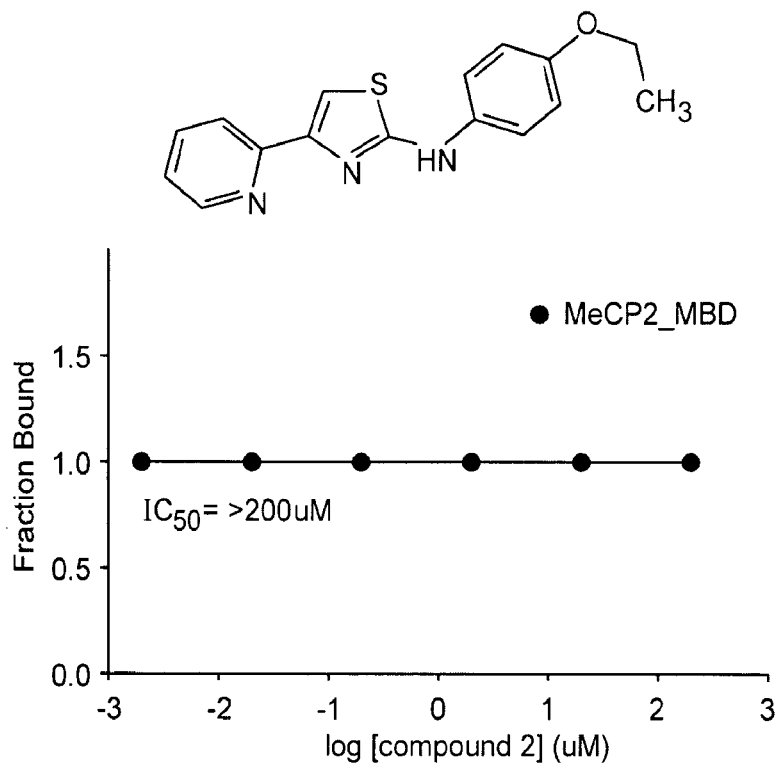
FIG. 23 is a graphical representation of the ability of a chemical compound to inhibit binding of the methyl-binding domain of MeCP2 to symmetrically methylated DNA oligonucleotides.
Figure 24:
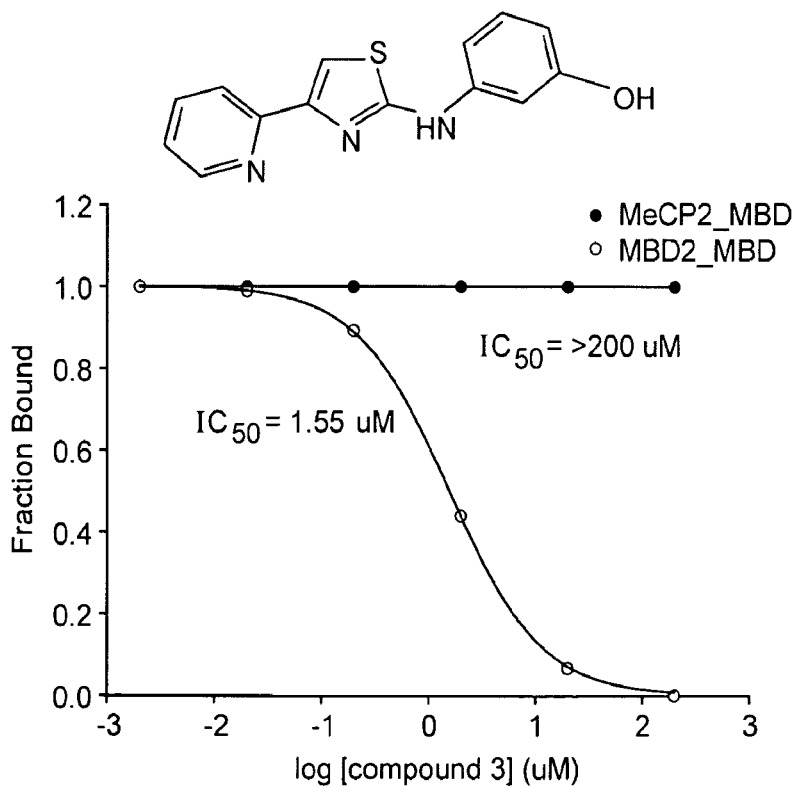
FIG. 24 is a graphical representation of the ability of a chemical compound to inhibit binding of the methyl-binding domain of MBD2 and MeCP2 to symmetrically methylated DNA oligonucleotides.
Figure 25:
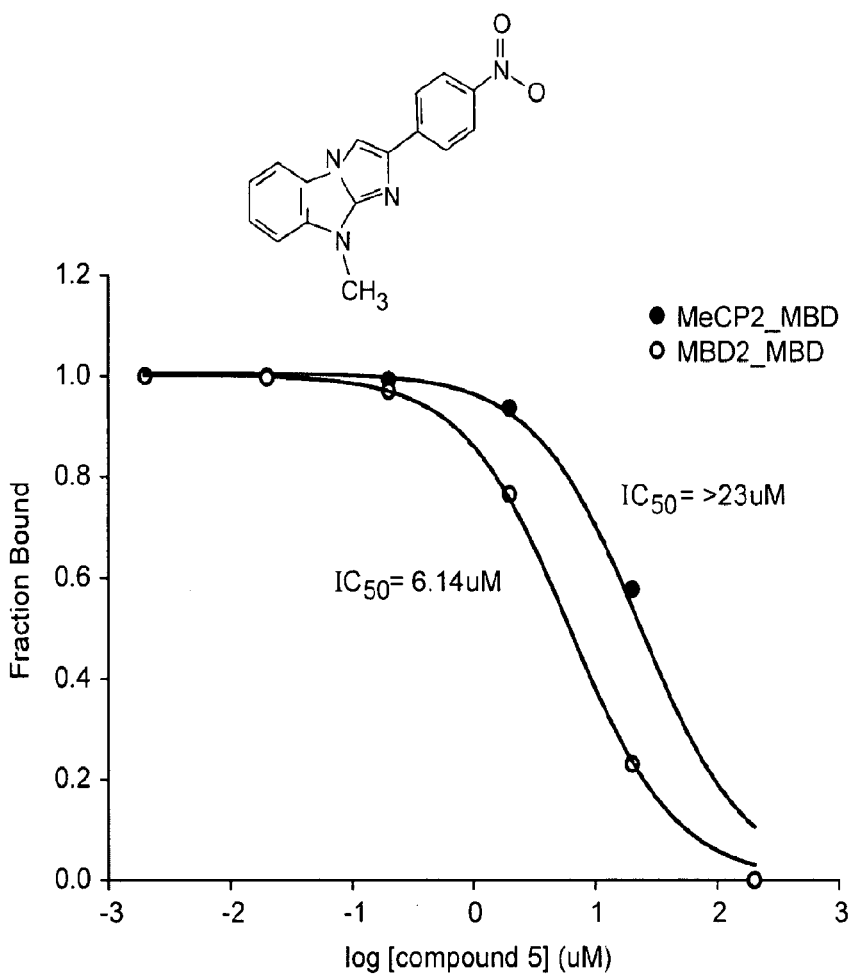
FIG. 25 is a graphical representation of the ability of a chemical compound to inhibit binding of the methyl-binding domain of MBD2 and MeCP2 to symmetrically methylated DNA oligonucleotides.
Figure 26:
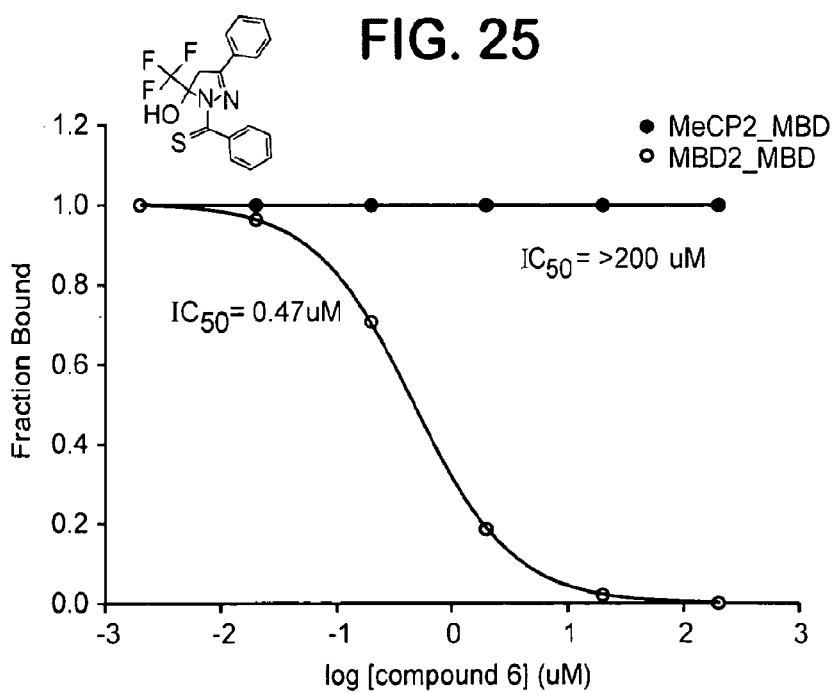
FIG. 26 is a graphical representation of the ability of a chemical compound to inhibit binding of the methyl-binding domain of MBD2 and MeCP2 to symmetrically methylated DNA oligonucleotides.
Figure 27:
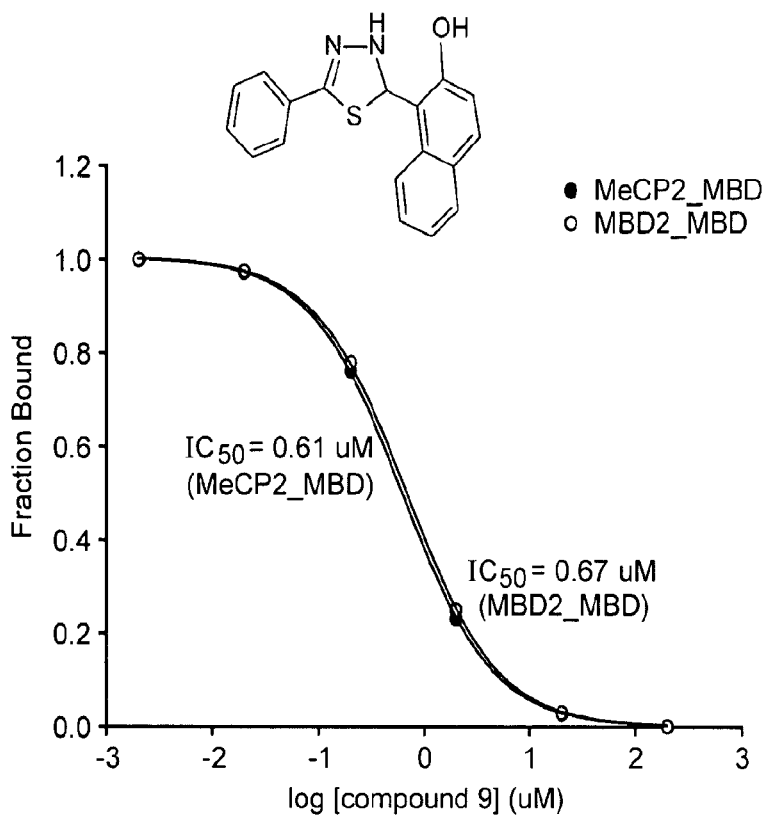
FIG. 27 is a graphical representation of the ability of a chemical compound to inhibit binding of the methyl-binding domain of MBD2 and MeCP2 to symmetrically methylated DNA oligonucleotides.
Figure 28:
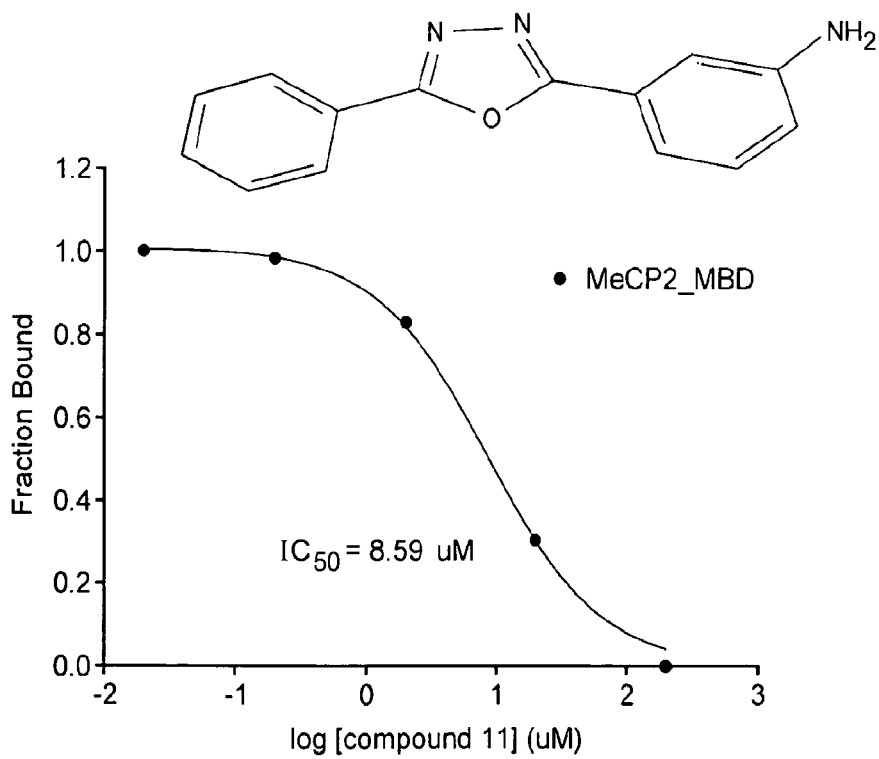
FIG. 28 is a graphical representation of the ability of a chemical compound to inhibit binding of the methyl-binding domain of MeCP2 to symmetrically methylated DNA oligonucleotides.
Figure 29:
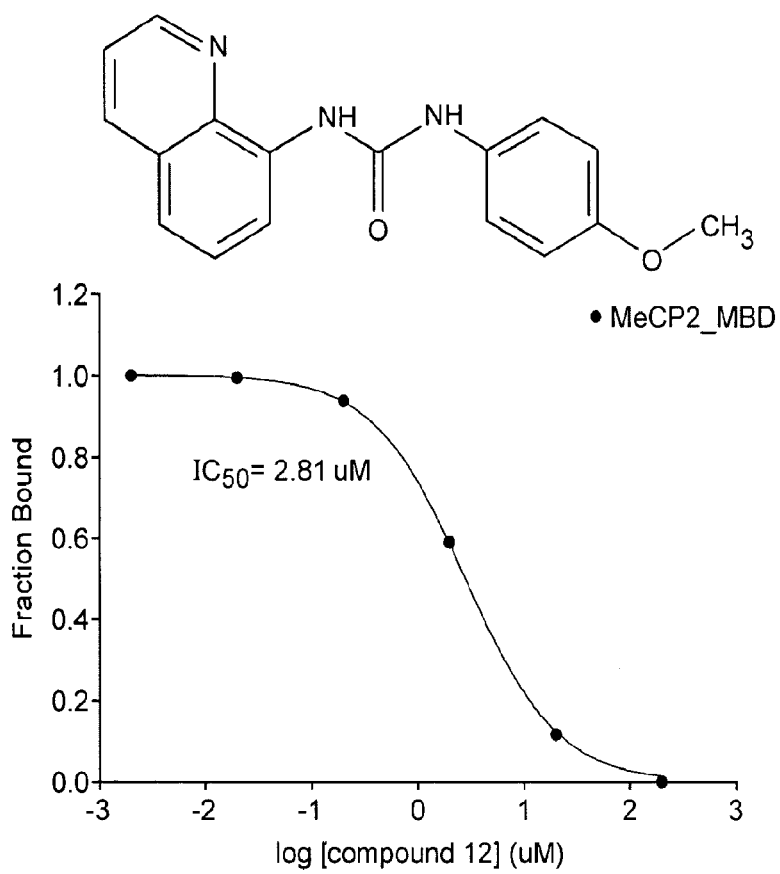
FIG. 29 is a graphical representation of the ability of a chemical compound to inhibit binding of the methyl-binding domain of MeCP2 to symmetrically methylated DNA oligonucleotides.
Figure 30:
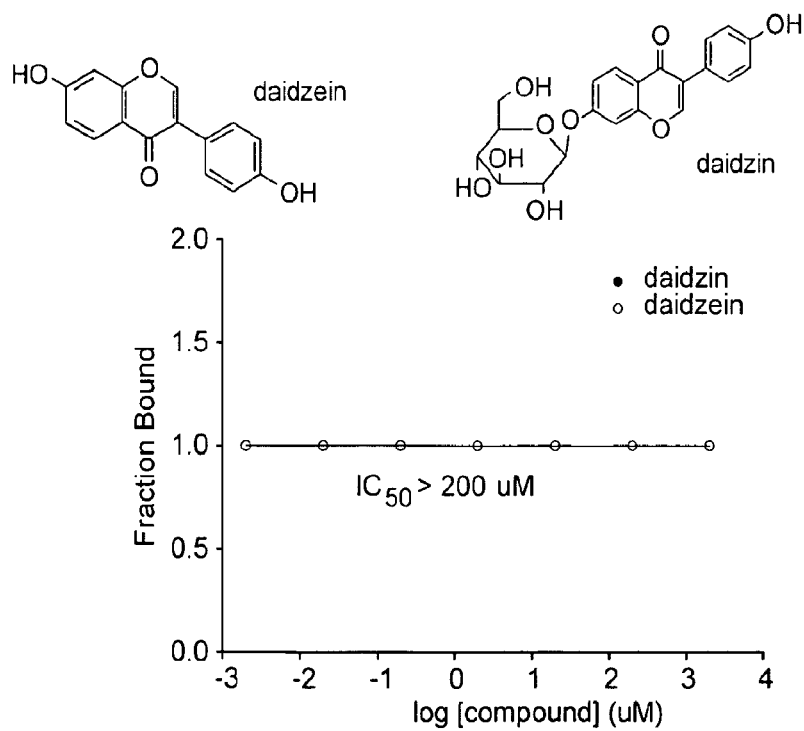
FIG. 30 is a graphical representation of inhibition binding assays of daidzein and daidzin with symmetrically methylated DNA oligonucleotides.
Figure 31:
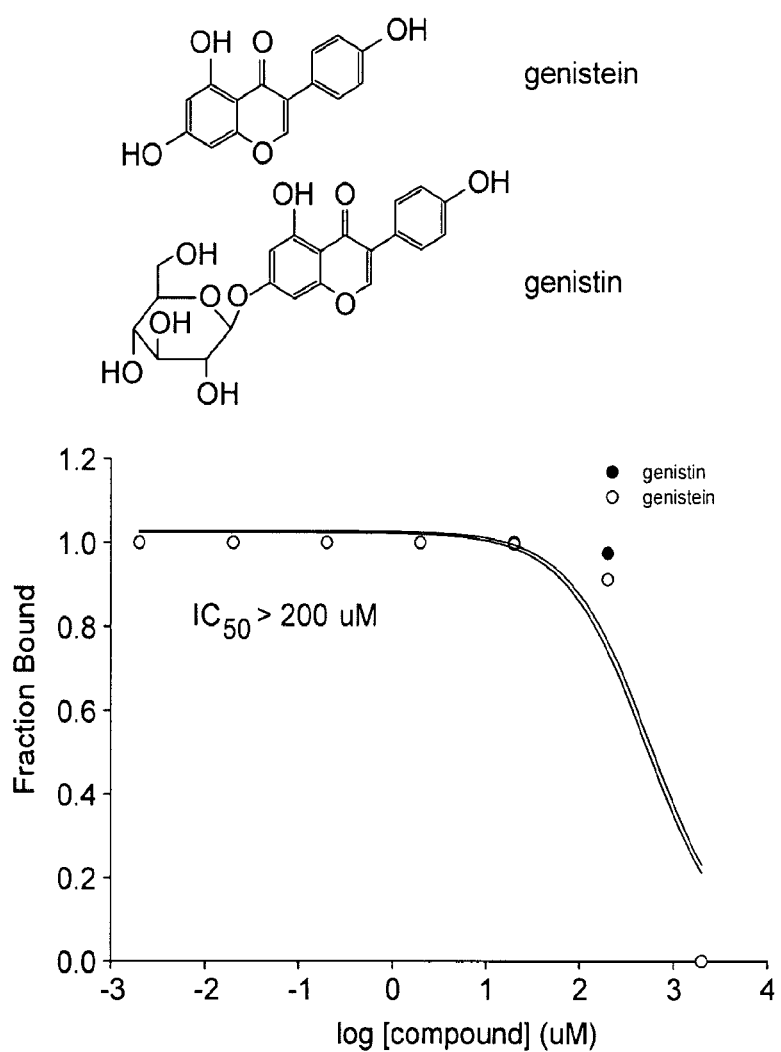
FIG. 31 is a graphical representation of inhibition binding assays of genistin and genistein with symmetrically methylated DNA oligonucleotides.

DNA methyltransferase activity assays were performed by combining 100 nM His$_{(6)}$-(SEQ ID NO:21)-DNMT with 5'-biotinylated synthetic hemi-methylated or unmethylated oligonucleotide substrate containing 1 μM CG (Top Strand 5'-GACGTCGTTCGTACGCTCGTTC-GACTCGTGCGACGGATCGGATTGTTATG-3' (SEQ ID NO:18), Bottom Strand 5'-CATAACAATCCGATCCGTCG-CACGAGTCGAACGAGCGTACGAACGACGTC-3' (SEQ ID NO:19)) and 1 μM S-adenosyl-L-[methyl-$^3$H]Methionine™ (Amersham TRK581 60-85 Ci/mmol). After incubation at 37° C. for 30 minutes, reactions were stopped by adding one volume of 10 mM cold S-adenosyl-L-Methionine™ (Sigma). To purify the oligonucleotides, reactions will be added to a SAm$^2$® 96 Biotin Capture Plate (Promega). The plate was washed 7 times with PBS+2M NaCl and 3 times with dH$_2$0 to remove His$_{(6)}$-(SEQ ID NO:21)-DNMT1 and S-adenosyl-L-methionine. After drying the plate, 30 μl Microscint-PS™ scintillation fluid (Packard) was added to each well, and tritium was quantitated using the TopCount™ NXT liquid scintillation counter (Packard). Using this approach, procainamide was found to inhibit DNMT1, via a mixed mechanism, with a K$_i$=7.2 μM, and to inhibit DNMT3a with a K$_i$=1.4 mM (FIGS. 18-20). Twelve of the 24 compounds have tested negative for DNMT1 inhibition.

Compounds that interfere with MBD binding to $^{5-me}$CpG-Containing DNA and/or reactivate epigenetically silenced gene expression are summarized in Table 2.

TABLE 2

| Compound | Structure | DNMT1 Binding Inhibition (IC$_{50}$ in μM) | MBD2 Binding Inhibition (IC$_{50}$ in μM) | MeCP2 Binding Inhibition (IC$_{50}$ in μM) | GSTP1 Re-expression Rank (+ to +++) |
|---|---|---|---|---|---|
| (I) | 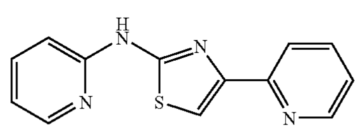 [SMILES: c1ccc(Nc2nc(-c3ccccn3)cs2)nc1] | No Inhibition | 1.55 | 10.46 | + |
| (II) | 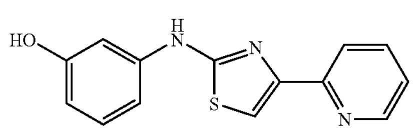 [SMILES: Oc1cccc(Nc2nc(-c3ccccn3)cs2)c1] | No Inhibition | 1.55 | >200 | + |
| (III) | 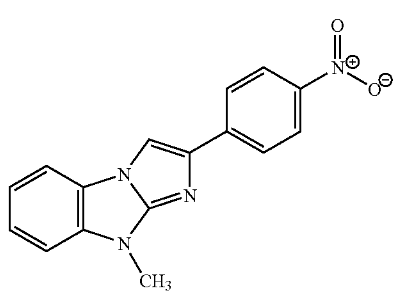 [SMILES: Cn1c2ccccc2n2cc(-c3ccc([N+](=O)[O-])cc3)nc12] | No Inhibition | 6.14 | >200 | +++ |

TABLE 2-continued

| Compound | Structure | DNMT1 Binding Inhibition (IC$_{50}$ in μM) | MBD2 Binding Inhibition (IC$_{50}$ in μM) | MeCP2 Binding Inhibition (IC$_{50}$ in μM) | GSTP1 Re-expression Rank (+ to +++) |
|---|---|---|---|---|---|
| (IV) | | Untested | Untested | Untested | +++ |
| (V) | 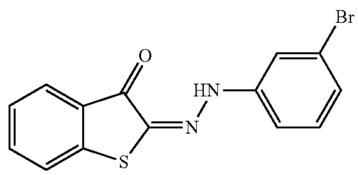 [SMILES: O=C1/C(=N\Nc2cccc(Br)c2)Sc2ccccc21] | Untested | Untested | Untested | +++ |
| (VI) | 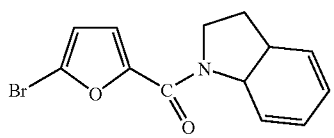 [SMILES: O=C(c1ccc(Br)o1)N1CCC2C=CC=CC21] | Untested | Untested | Untested | +++ |
| (VII) | 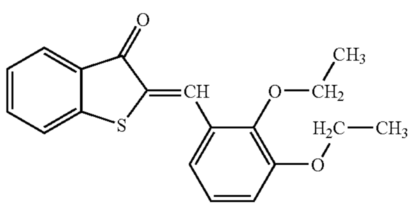 [SMILES: CCOc1cccc(/C=C2\Sc3ccccc3C2=O)c1OCC] | Untested | Untested | Untested | +++ |
| (VIII) | 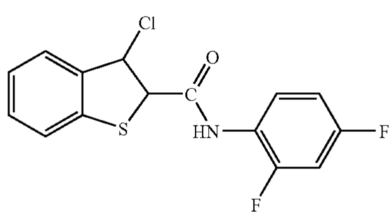 [SMILES: O=C(Nc1ccc(F)cc1F)C1Sc2ccccc2C1Cl] | Untested | Untested | Untested | +++ |
| (IV) | | Untested | Untested | Untested | +++ |
| (X) | 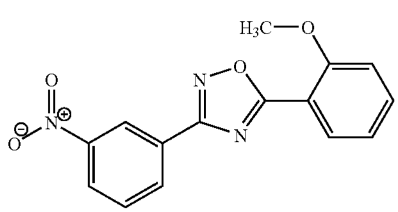 [SMILES: COc1ccccc1-c1nc(-c2cccc([N+](=O)[O-])c2)no1] | No Inhibition | Untested | >200 | +++ |

TABLE 2-continued

| Compound | Structure | DNMT1 Binding Inhibition (IC$_{50}$ in μM) | MBD2 Binding Inhibition (IC$_{50}$ in μM) | MeCP2 Binding Inhibition (IC$_{50}$ in μM) | GSTP1 Re-expression Rank (+ to +++) |
|---|---|---|---|---|---|
| (XI) | 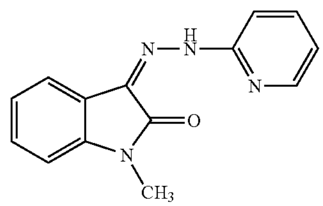 [SMILES: CN1C(=O)/C(=N\Nc2ccccn2)c2ccccc21] | Untested | Untested | Untested | +++ |
| (XII) | 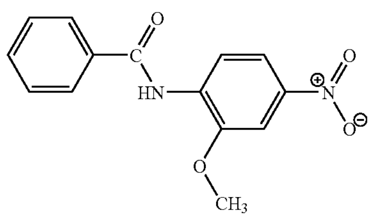 [SMILES: COc1cc([N+](=O)[O-])ccc1NC(=O)c1ccccc1] | Untested | Untested | Untested | +++ |
| (XIII) | 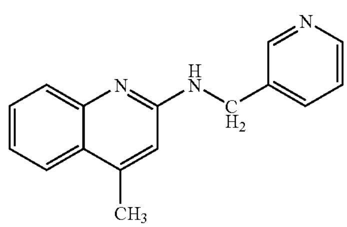 [SMILES: Cc1cc(NCc2cccnc2)nc2ccccc12] | Untested | Untested | Untested | +++ |
| (XIV) | 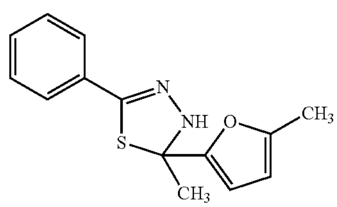 [SMILES: Cc1ccc(C2(C)NN=C(c3ccccc3)S2)o1] | Untested | Untested | Untested | +++ |
| (XV) | 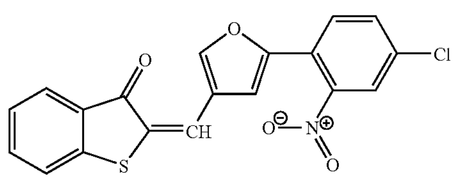 [SMILES: O=C1/C(=C\c2coc(-c3ccc(Cl)cc3[N+](=O)[O-])c2)Sc2ccccc21] | Untested | Untested | Untested | +++ |
| (XVI) | 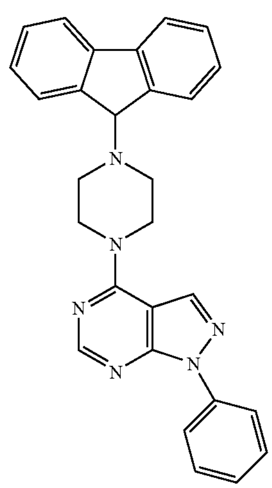 [SMILES: c1ccc(-n2ncc3c(N4CCN(C5c6ccccc6-c6ccccc65)CC4)ncnc32)cc1] | Untested | Untested | Untested | +++ |

TABLE 2-continued

| Compound | Structure | DNMT1 Binding Inhibition (IC$_{50}$ in µM) | MBD2 Binding Inhibition (IC$_{50}$ in µM) | MeCP2 Binding Inhibition (IC$_{50}$ in µM) | GSTP1 Re-expression Rank (+ to +++) |
|---|---|---|---|---|---|
| (XVII) | 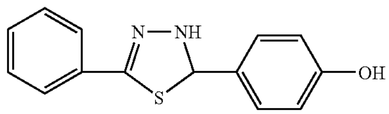 [SMILES: Oc1ccc(C2NN=C(c3ccccc3)S2)cc1] | No Inhibition | 0.011 | 16.9 | +++ |
| (XVIII) | 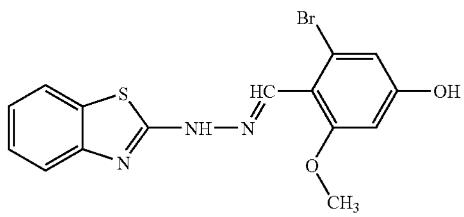 [SMILES: COc1cc(O)cc(Br)c1/C=N/Nc1nc2ccccc2s1] | No Inhibition | 38 | >200 | +++ |
| (XIX) | 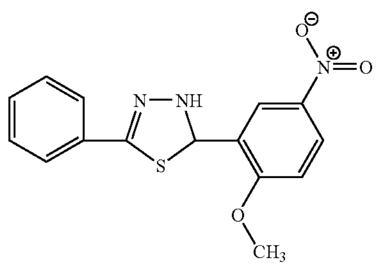 [SMILES: COc1ccc([N+](=O)[O-])cc1C1NN=C(c2ccccc2)S1] | No Inhibition | In-conclusive | | |
| (XX) | 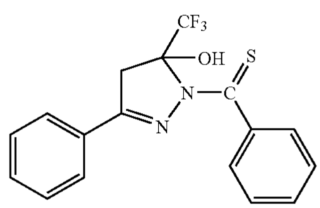 [SMILES: OC1(C(F)(F)F)CC(c2ccccc2)=NN1C(=S)c1ccccc1] | No Inhibition | 0.47 | >200 | + |
| (XXI) | 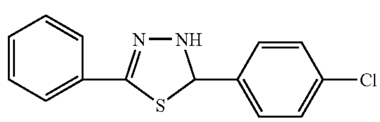 [SMILES: Clc1ccc(C2NN=C(c3ccccc3)S2)cc1] | No Inhibition | 0.21 | 33.9 | + |
| (XXII) | 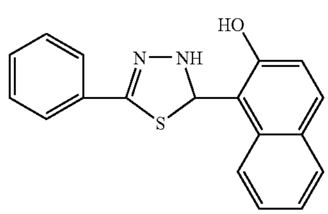 [SMILES: Oc1ccc2ccccc2c1C1NN=C(c2ccccc2)S1] | No Inhibition | 0.67 | 0.61 | + |
| (XXIII) | 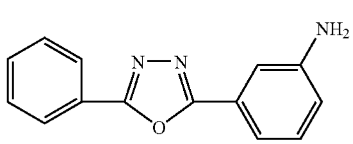 [SMILES: Nc1cccc(-c2nnc(-c3ccccc3)o2)c1] | No Inhibition | Untested | 8.59 | + |
| (XXIV) | 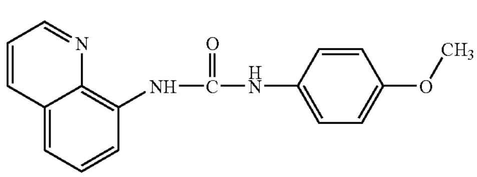 [SMILES: COc1ccc(NC(=O)Nc2cccc3cccnc23)cc1] | No Inhibition | Untested | 2.81 | + |

TABLE 2-continued

| Compound | Structure | DNMT1 Binding Inhibition (IC$_{50}$ in µM) | MBD2 Binding Inhibition (IC$_{50}$ in µM) | MeCP2 Binding Inhibition (IC$_{50}$ in µM) | GSTP1 Re-expression Rank (+ to +++) |
|---|---|---|---|---|---|
| (XXV) | 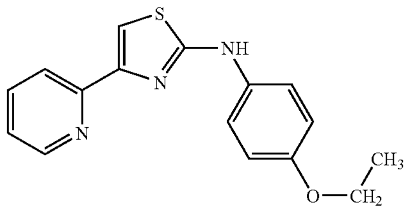 [SMILES: CCOc1ccc(Nc2nc(-c3ccccn3)cs2)cc1] | | | >200 | |

What is claimed is:

1. A method of treating prostate cancer in a subject, comprising administering to the subject a methylbinding domain (MBD) pathway antagonist of structural Formula III:

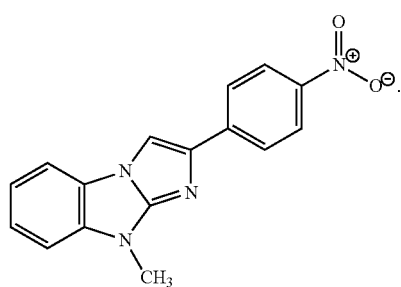

III

2. The method of claim 1, wherein the prostate cancer is metastatic prostate cancer.

3. The method of claim 1, wherein the subject is a human.

4. The method of claim 1, wherein the MBD pathway antagonist inhibits interaction of MBD2 with methylated genomic DNA.

5. The method of claim 1, wherein the MBD pathway antagonist reduces methyl binding domain protein 2 (MBD2) activity.

6. The method of claim 5, wherein the MBD pathway antagonist reactivates expression of GSTP1 gene having CpG island hypermethylation.

7. The method of claim 6, wherein the antagonist inhibits interaction of MBD2 with methylated genomic DNA.

8. The method of claim 1, wherein the MBD pathway antagonist reduces methyl CpG binding protein 2 (MeCP2) activity.

* * * * *